US012630850B2

(12) United States Patent
Senger et al.

(10) Patent No.: US 12,630,850 B2
(45) Date of Patent: May 19, 2026

(54) ENZYMATIC BREAK DOWN OF CHLOROGENIC ACID IN SUNFLOWER-CONTAINING PRODUCTS

(71) Applicant: Chapman University, Orange, CA (US)

(72) Inventors: Lilian Senger, Orange, CA (US); Cedric Owens, Orange, CA (US); Christine Lo Verde, Orange, CA (US)

(73) Assignee: Chapman University, Orange, CA (US)

( * ) Notice: Subject to any disclaimer, the term of this patent is extended or adjusted under 35 U.S.C. 154(b) by 377 days.

(21) Appl. No.: 18/345,757

(22) Filed: Jun. 30, 2023

(65) Prior Publication Data

US 2024/0141393 A1 May 2, 2024

Related U.S. Application Data

(60) Provisional application No. 63/357,518, filed on Jun. 30, 2022.

(51) Int. Cl.
| | |
|---|---|
| *C12P 7/42* | (2006.01) |
| *A21D 2/26* | (2006.01) |
| *C12N 9/16* | (2006.01) |

(52) U.S. Cl.
CPC ............... *C12P 7/42* (2013.01); *A21D 2/267* (2013.01); *C12N 9/16* (2013.01); *C12Y 301/01073* (2013.01)

(58) Field of Classification Search
CPC .... C12P 7/42; C12N 9/16; C12N 9/20; A21D 8/042
See application file for complete search history.

(56) References Cited

PUBLICATIONS

Zhang et al. Biotechnol Lett (2019) 41:565-574. (Year: 2019).*
Atonfack, J. T., Ataman, Z. A., & Were, L. M. (2019). Acidulant effect on greening, reducing capacity, and tryptophan fluorescence of sunflower butter cookie dough during refrigerated storage. J. Sci. Food. Agric., 99 (5), 2186-2193.
Benoit, I., Asther, M., Bourne, Y., Navarro, D., Canaan, S., Lesage-Meessen, L., Herweijer, M., Coutinho, P. M., Asther, M., & Record, E. (2007). Gene overexpression and biochemical characterization of the biotechnologically relevant chlorogenic acid hydrolase from Aspergillus niger. Appl Environ Microbiol, 73 (17), 5624-5632.
Chahinian, H., Ali, Y. B., Abousalham, A., Petry, S., Mandrich, L., Manco, G., Canaan, S., & Sarda, L. (2005). Substrate specificity and kinetic properties of enzymes belonging to the hormone-sensitive lipase family: comparison with non-lipolytic and lipolytic carboxylesterases. Biochim Biophys Acta, 1738 (1-3), 29-36.
Fritsch, C., Jansch, A., Ehrmann, M. A., Toelstede, S., & Vogel, R. F. (2017). Characterization of Cinnamoyl Esterases from Different Lactobacilli and Bifidobacteria. Curr Microbiol, 74 (2), 247-256.
Gonzalez-Perez, S., Merck, K. B., Vereijken, J. M., van Koningsveld, G. A., Gruppen, H., & Voragen, A. G. (2002). Isolation and characterization of undenatured chlorogenic acid free sunflower (Helianthus annuus) proteins. J Agric Food Chem, 50 (6), 1713-1719.
Grasso, S., Liu, S. Y., & Methven, L. (2020). Quality of muffins enriched with upcycled defatted sunflower seed flour. Lwt-Food Science and Technology, 119.
Ishii, A. K., Toto Pacioles, C., & Were, L. (2021). Color and structural modifications of alkaline extracted sunflower protein concentrates and isolates using L-cysteine and glutathione. Food Res Int, 147, 110574.
Kumar, R. S., Brannigan, J. A., Prabhune, A. A., Pundle, A. V., Dodson, G. G., Dodson, E. J., & Suresh, C. G. (2006). Structural and functional analysis of a conjugated bile salt hydrolase from Bifidobacterium longum reveals an evolutionary relationship with penicillin V acylase. J Biol Chem, 281 (43), 32516-32525.
Lai, K. K., Lorca, G. L., & Gonzalez, C. F. (2009). Biochemical Properties of Two Cinnamoyl Esterases Purified from a Lactobacillus johnsonii Strain Isolated from Stool Samples of Diabetes-Resistant Rats. Appl Environ Microbiol, 75 (15), 5018-5024.
Lai, K. K., Stogios, P. J., Vu, C., Xu, X., Cui, H., Molloy, S., Savchenko, A., Yakunin, A., & Gonzalez, C. F. (2011). An Inserted alpha/beta Subdomain Shapes the Catalytic Pocket of Lactobacillus johnsonii Cinnamoyl Esterase. PLoS One, 6 (8).
Liang, S., Tran, H. L., & Were, L. (2018). Lowering greening of cookies made from sunflower butter using acidic ingredients and effect on reducing capacity, tryptophan and protein oxidation. Food Chem, 252, 318-326.
Liang, Y., & Were, L. (2020). Cysteine's effects on chlorogenic acid quinone induced greening and browning: Mechanism and effect on antioxidant reducing capacity. Food Chem, 309, 125697.
Medina, M. S., Bretzing, K. O., Aviles, R. A., Chong, K. M., Espinoza, A., Garcia, C. N. G., Katz, B. B., Kharwa, R. N., Hernandez, A., Lee, J. L., Lee, T. M., Lo Verde, C., Strul, M. W., Wong, E. Y., & Owens, C. P. (2021). CowN sustains nitrogenase turnover in the presence of the inhibitor carbon monoxide. J Biol Chem, 296, 100501.
Pickardt, C., Neidhart, S., Griesbach, C., Dube, M., Knauf, U., Kammerer, D. R., & Carle, R. (2009). Optimisation of mild-acidic protein extraction from defatted sunflower (Helianthus annuus L.) meal. Food Hydrocoll., 23 (7), 1966-1973.
Singleton, R., V., & Rossi, A. J. (1965). Colorimetry of total phenolics with phosphomolybdic-phosphotungstic acid reagents. Am J Enol Vitic, 14, 144-158.
Song, Y. R., & Baik, S. H. (2017). Molecular cloning, purification, and characterization of a novel thermostable cinnamoyl esterase from Lactobacillus helveticus KCCM 11223. Prep. Biochem. Biotechnol., 47 (5), 496-504.
Wianowska, D., & Gil, M. (2019). Recent advances in extraction and analysis procedures of natural chlorogenic acids. Phytochemistry Rev., 18, 273-302.
Zhang, W. B., Liu, Y. C., Hu, M. J., & Yang, R. J. (2019). Preparation of high-quality sunflower seed protein with a new chlorogenic acid hydrolase from Aspergillus niger. Biotechnol. Lett., 41 (4-5), 565-574.

* cited by examiner

*Primary Examiner* — Tekchand Saidha
(74) *Attorney, Agent, or Firm* — K&L Gates LLP; Brian J. Novak; Giorgios N. Kefallinos

(57) ABSTRACT

Disclosed herein are methods of reducing and/or preventing "greening" in sunflower-containing food products.

20 Claims, 20 Drawing Sheets
(4 of 20 Drawing Sheet(s) Filed in Color)

Specification includes a Sequence Listing.

```
L. johnsonii      ------------MATITLERDGLQLVGTREEPFGEIYDMAIIFHGFTANRNTSLLKEIANS
L. gasseri        MKLKKKKVGIYMATITIERDGLNLVGTREEPFGEIYDMAIIFHGFTANRNTPLLKEIADE
L. helveticus     ------------MSRITIERDGLTLVGDREEPFGEIYDMAIIMHGFAANRNTDLLRQIADD
L. acidophilus    ------------MSRITIERDGLTLVGDREEPFGEIYDMAILMHGFTANRNTPLLRQIADN
                             *; **;***** *** **************;;***;***** **.;**;.

L. johnsonii      LRDENIASVRFDFNGHGDSDGKFENMTVLNEIEDANAILNYVKTDPHVRNIYLVGHSQGG
L. gasseri        LRDENIASVRFDFNGHGDSDGKFENMTVLNEIEDANAILNYVKTDPHVRNIYLVGHSQGG
L. helveticus     LRDENVASVRFDFNGHGESDGKFEDMTVCNEIADGKAILDYVRTDPHVRDIFLVGHSQGG
L. acidophilus    LRDENVASVRFDFNGHGESDGAFEDMTVCNEIADAQKILEYVRTDPHVRNIFLVGHSQGG
                  *****;************;*** **;*** *** *.; **;**.******;*;********

L. johnsonii      VVASMLAGLYPDLIKKVVLLAPAATLKSDALEGNTQGVTYNPDHIPDRLPFKDLTLG---
L. gasseri        VVASMLAGLYPDIIKKVVLLAPAATLKTDALNGSTQGVKYNPDHIPDRLPFKDLTLG---
L. helveticus     VVASMLAGLYPDVVKKVVLLAPAAQLKDDALRSNTQGATYDPNHIPDVVPLVGNKLGMKL
L. acidophilus    VVASMLAGLYPDIVKKVVLLAPAAQLKDDALNGDTQGATYNPEHIPAAIPFHGKKLG---
                  ************;;********** ** *** .,***..*;*;*** ;*; . .**

L. johnsonii      -GFYLRIAQQLPIYEVSAQFTKPVCLIHGTDDTVVSPNASKKYDQIYQNSTLHLIEGADH
L. gasseri        -GFYLRIAQQLPIYEVSVHFTRPVCLIHGANDTVVSPDASKKYDQVYENSTLHLVEGADH
L. helveticus     GGFYLRTAQVLPIYEVSQCFTRPVSIAGTNDQVVDPKYAKKYDEVYENSELHMIPNADH
L. acidophilus    -GFYLRTAQVLPIYEIAKHYTNPVSIIVGSNDQVVAPKYSKKYDEVYENSELHMVPDADH
                  ***** ** *****;;   ;*.**.;* *;;* ** *. ;****;;*;** **;; .***

L. johnsonii      CFSDSYQKNAVNLTTDFLQNNNAF
L. gasseri        SFTDTYQKTAADLTAEFLQDNNTF
L. helveticus     RFSGGYKDMAADLTAQFLKP--AF
L. acidophilus    SFTGQYKDSAVDLTAEFLKP--LF
                  *;. *;. *.;**;;**;    *
```

FIG. 2A

Extended insertion
domain loop

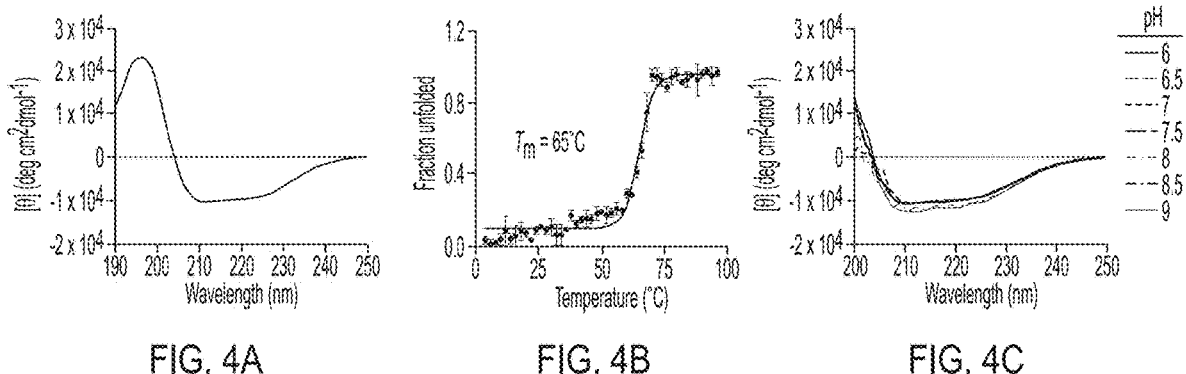
FIG. 4A                    FIG. 4B                    FIG. 4C

FIG. 13A                    FIG. 13B

| | Storage time | | |
|---|---|---|---|
| | 1 h | 3 h | 24 h |
| Control (no CGA esterase) | | | |
| CIE a* | 4.80 ± 1.29 | 5.16 ± 1.31 | -0.07 ± 0.69 |
| Browning Index | 51.09 ± 5.31 | 52.26 ± 2.52 | 35.77 ± 2.30 |
| Pretreated Flour (0.090 mg CGA esterase/1 g flour) | | | |
| CIE a* | 9.70 ± 0.05 | 9.68 ± 0.23 | 9.84 ± 1.25 |
| Browning Index | 60.09 ± 1.32 | 59.78 ± 2.22 | 58.12 ± 1.58 |
| Direct Treatment Flour (0.090 mg CGA esterase/1 g flour) | | | |
| CIE a* | 8.95 ± 0.41 | 8.66 ± 0.83 | 8.00 ± 0.56 |
| Browning Index | 54.10 ± 4.99 | 44.12 ± 0.08 | 50.58 ± 0.86 |

FIG. 15

Nutrition Facts

Servings per container
Serving size                    (23g)

Amount per serving
Calories                    90

% Daily Value

Total Fat 5g

Saturated Fat 1g

Trans Fat 0g

Cholesterol 10mg

Sodium 90mg

Total Carbohydrate 9g

Dietary Fiber 0g

Total Sugars 6g

Includes 6g Added Sugars

Protein 2g

Vitamin D 0mcg

Calcium 0mg

Iron 1mg

Potassium 15mg

INGREDIENTS: Sunflower seed flour, unsalted butter, egg, brown sugar, maple syrup, baking soda, salt, vanilla extract.

CONTAINS: Egg.

Upcycled sunflower flour for use in baking

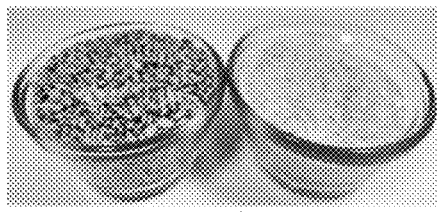

Sunflower seeds ➡ Sunflower flour

Benefits of sunflower flour

- High in protein
- High in Antioxidants
- Gluten & soy free
- Allergen-free
- Nut-free
- GMO free/Organic Sunflower flour is a byproduct of sunflower oil production and is mainly discarded or used as animal feed. However, sunflower flour is packed with nutrients and is allergen-free. Instead of discarding the flour, we are upcycling it to make baked foods such as the cookies you are about to taste.

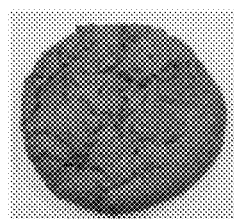

FIG. 17

ENZYMATIC BREAK DOWN OF CHLOROGENIC ACID IN SUNFLOWER-CONTAINING PRODUCTS

CROSS-REFERENCE TO RELATED APPLICATION

This application claims the benefit of, and priority to, U.S. Provisional Patent Application 63/357,518 filed Jun. 30, 2022, the entire contents of which is incorporated by reference herein.

GOVERNMENT RIGHTS

This invention was made with government support funded by a National Institute of Food and Agriculture award (2020-67018-31261). The government has certain rights in the invention.

BACKGROUND

Chlorogenic acid (CGA) is a phenolic compound widely found in fruits and vegetables (apples, pears, carrots, tomatoes, and sweet potatoes) as well as coffee and tea. It is found in many foods and reacts with free amino groups in proteins at alkaline pH. Sunflower seeds contain a high concentration of CGA, which reacts with amino acids to form green pigments under alkaline conditions during food processing, a process known as "greening." Current methods of preventing greening do not sufficiently address the problem.

SUMMARY

The disclosed embodiments enable more widespread use of sunflower-derived products in applications where neutrally-colored food products are desired.

Disclosed embodiments comprise methods of preventing or reducing discoloration associated with food processing of sunflower-derived products, such discoloration including greening in foods.

Disclosed methods can comprise contacting or treating a sunflower-derived dough with a CGA esterase.

Thus, disclosed herein are methods for hydrolyzing chlorogenic acid (CGA) in a sunflower seed-containing product comprising treating the sunflower seed-containing product with a CGA esterase. In some embodiments, the sunflower seed-containing product comprises sunflower meal, sunflower butter, or a sunflower protein product.

In some embodiments, the treating comprises contacting a dough containing sunflower meal, sunflower butter, or sunflower protein product with a CGA esterase or contacting the sunflower meal, sunflower butter, or sunflower protein product directly.

In some embodiments, treatment of the sunflower seed-containing product with a CGA esterase lessens the greening of bakery goods produced from the sunflower seed-containing product.

In some embodiments, the CGA esterase is from a *Bacillus* species. In some embodiments, the CGA esterase is from a *Lactobacillus* species. In some embodiments, the CGA esterase is from *Lactobacillus helveticus*.

In some embodiments, treating comprises addition of less than 100 ppm of CGA esterase to the sunflower seed-containing product.

In some embodiments, the sunflower seed-containing product is a incorporated into a food product. In some embodiments, the sunflower seed-containing product is incorporated into a baked food product. In some embodiments, the baked food product comprises cookies, bread, or muffins.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A: Sequence alignment of various CGA esterases from the genus *Lactobacillus*: *L. johnsonii* (SEQ ID NO:3), *L. gasseri* (SEQ ID NO:4), *L. helveticus* (SEQ ID NO:5), *L. acidophilus* (SEQ ID NO:6). Asterisks denote conserved residues.

FIG. 4A: Circular dichroism (CD) spectrum of CGA esterase at room temperature (21° C.), suggesting a mixture of $\alpha$-helices and $\beta$-sheets. FIG. 4B: Thermal denaturation curve of CGA esterase. FIG. 4C: Room temperature (21° C.) CD spectra of CGA esterase at pH 6.0-9.0, indicating that the protein is stable over a wide range of pH.

FIG. 10B: the reaction was stopped with HCl after 2 min, and the peak at 5.4 min is indicative of caffeic acid.

FIG. 11: Representative sunflower meal (SFM) HPLC chromatograms of the FIG. 11A pellet and FIG. 11B supernatant in presence and absence of CGA esterase. Phenolic compounds were monitored at 320 nm. Asterisks represent other compounds in the SFM that are neither CGA nor CA.

FIG. 15: Internal greening of cookies formulated and baked with sunflower flour following pretreatment of flour with CGA esterase or direct addition of the enzyme during the dough preparation compared to a control without enzyme.

FIG. 17: Concept card provided to the panelists at the beginning of the study. The nutrition label was made using Genesis R&D.

DETAILED DESCRIPTION

Figures 1A, 1B:
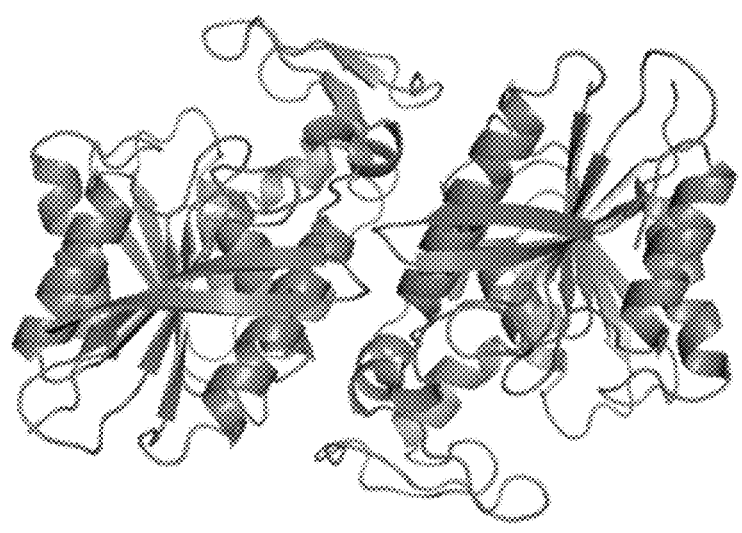
FIG. 1A: Proposed reaction mechanisms for CGA breakdown in sunflower-derived ingredients and CGA-induced greening.

Chlorogenic acid (CGA) is a polyphenolic compound present in several foods, such as sunflower seeds and unroasted coffee beans. While CGA is considered beneficial to human health for its antioxidant properties, high concentrations of CGA are problematic in sunflower products because under alkaline conditions CGA reacts with free amines in proteins, forming a dark, aesthetically displeasing green trihydroxybenzacridine pigment (FIG. 1A).

The majority (approx. 60%) of sunflower seeds are used for sunflower oil production. The meal that remains after oil pressing is rich in nutrients such as protein and phenolics. However, most sunflower meal (SFM) is currently discarded, used as fertilizer, or as animal fodder. Using SFM as a source material to produce sunflower proteins (SPI) and sunflower flour would increase its utility. The main obstacle to utilizing SFM more widely is the high concentration of CGA in sunflower seeds. CGA constitutes up to 70% of all phenolic compounds or approximately 1.4% of dry weight, causing the aforementioned greening reaction as CGA reacts with sunflower proteins under alkaline conditions.

This greening reaction means that lightly colored sunflower proteins must currently be processed using acidic extraction instead of higher-yielding alkaline isoelectric precipitation methods. Greening also prevents the use of SFM for applications where high pH is used and neutral colors are preferred, such as for baking cookies, bread, and muffins.

CGA esterase is a hydrolase that breaks down CGA into caffeic and quinic acid. The enzyme features a typical a/P hydrolase fold and cleaves CGA using a Ser-His-Asp catalytic triad. CGA esterases are part of the large ferulic acid esterase family of enzymes (EC 3.1.1.73) that are characterized by their ability to hydrolyze alkyl chain esters of hydroxycinnamic acid derivatives. Although all ferulic acid esterases feature an a/P hydrolase fold, they are diverse in structure, substrate specificity, and active site architecture. CGA esterases have been discovered in both bacterial and fungal species, notably among the fungal genus *Aspergillus* and the bacterial genus *Lactobacillus*. Bacterial and fungal CGA esterases differ substantially from each other in terms of sequence and structure. Structural analysis using the DALI protein structure comparison server (Holm, 2020) indicates that bacterial CGA esterases are most similar to human monoglyceride lipases and bacterial peroxidases. The main structural feature characteristic of bacterial CGA esterases is an a/P insertion domain in proximity to the active site (FIG. 1B), which is absent in all known fungal counterparts. Furthermore, unlike fungal CGA esterases, the bacterial enzymes are not glycosylated and therefore easier to express recombinantly in bacteria.

Fungal CGA esterases have received significant attention for their biotechnological potential. In addition to being active against CGA, they are able to release hydrocinnamic acid derivatives from the cell wall of plants and are therefore of great interest to the pulp and paper and biomass processing industries. Compared to fungal CGA esterases, the functional potential of bacterial CGA esterases remains unexplored. While some kinetic and enzymatic properties of CGA esterase from *L. helveticus, L. gasseri, L. acidophilus, L. plantarum,* and *L. johnsonii* were reported, bacterial CGA esterases have yet to be tested in food applications.

Because the CGA concentration in sunflower seeds is high, preventing CGA-induced greening in sunflower seed-derived products has been challenging. Several attempts have been reported in the literature, however, none are fully satisfactory. For example, it is possible to extract CGA using organic solvents such as methanol or obtain sunflower proteins by membrane filtration (Gonzalez-Perez et al., 2002; Pickardt et al., 2009; Wianowska & Gil, 2019).

However, these approaches remove beneficial phenolics present in sunflower seeds and introduce the problems of solvent recovery, cost, and safety. Attempts to mitigate greening in SPI and solutions by altering redox conditions using cysteine have been successful (Ishii et al. 2021; Y. Liang & Were, 2020), but this approach only works when cysteine levels are high (above 2.1 mM) and is not compatible with foods that carry a "clean label" claim. Finally, a study by Zhang et al. (2019) attempted to hydrolyze CGA and prevent greening using a fungal CGA esterase from *Aspergillus niger*. The study indicated that *A. niger* CGA esterase hydrolyzed CGA, however, there was no direct evidence of enzymatic greening prevention since the SFM was partially de-phenolized by organic solvent extraction and the experiment was conducted entirely at acidic pH, which in and of itself mitigates greening (Atonfack et al. 2019; S. Liang et al. 2018). In addition to the lack of evidence for greening prevention, CGA esterase's enzymatic and physical properties in food matrices are nearly uncharacterized.

Disclosed herein is the biochemical characterization and application of a highly active chlorogenic acid esterase from *Lactobacillus helveticus*. The enzyme is the most active CGA esterase known to date with a $K_m$ of 0.090 mM and a $k_{cat}$ of 82 s$^{-1}$. The CGA esterase is easily expressed recombinantly in *E. coli* in large yields and is stable over a wide range of pH and temperatures.

We further characterized CGA esterase's kinetic properties in sunflower meal and demonstrated that the enzyme completely hydrolyzes CGA in the meal. Finally, we showed that CGA esterase treatment of sunflower seed meal enables production of pale brown sunflower protein isolates using alkaline extraction. This work will enable more widespread use of sunflower-derived products in applications where neutrally-colored food products are desired.

Here, we present an approach to prevent green pigment formation in, for example, sunflower cookies by:

a. hydrolyzing CGA into caffeic acid and quinic acid with a CGA esterase from *L. helveticus*.

CGA esterase hydrolyzed CGA in both sunflower butter and flour, resulting in the complete elimination of greening in the sunflower cookies. CGA esterase treatment was efficient as the enzyme could be applied in low amounts (<100 ppm) directly to the dough without needing to pretreat either sunflower butter or flour. Overall, our data indicate that CGA esterase treatment was an effective method of eliminating unwanted greening in sunflower cookies.

Disclosed herein is the concept that a *Lactobacillus* CGA esterase will be highly effective at removing CGA from SFM and preventing greening in SPI. We demonstrate that CGA esterase from *L. helveticus* is the best-performing CGA esterase known to date. We show that the enzyme is efficiently expressed in *E. coli*, is very stable and active under a wide range of conditions, and that CGA esterase breaks down CGA in SFM. Finally, we demonstrate that CGA esterase treatment enables production of light-brown sunflower-seed derived meal and protein powders.

Sunflower seed products such as seed flour, butter, oil, or protein isolates are allergen-free substitute ingredients for wheat, soy, and peanut products, which have allergenic properties. In addition, sunflower seeds are a rich source of phenolic compounds, which make up to 4% of the seed on a dry weight basis. The most prevalent phenolic compound in sunflower seeds is the hydrocinnamic acid derivative, chlorogenic acid (CGA), which is an ester of caffeic acid (CA) and quinic acid (QA), representing the major phenolic compound in sunflower seed. The presence of CGA in sunflower seeds gives rise to a green pigment during processing under alkaline conditions. Formation of the green pigment occurs when the catechol moiety of CGA is oxidized to form an o-quinone intermediate, which is electron-deficient and readily reacts with nucleophilic amines in proteins.

CGA quinone-induced color formation is a major factor hindering the use of sunflower butter and flour in consumer food products. Sunflower is primarily produced as an economically important oilseed crop, with approximately 60% of sunflower being produced globally for oil production. The sunflower meal, a byproduct obtained after oil production, is used for animal feed, fertilizer, or energy production. Prevention of CGA quinone-induced color formation could add value to sunflower and increase its use in consumer food products, for example, by milling the meal into flour for baking.

Esterases are part of the hydrolase class of enzymes, which are widely used in food processing applications, including in the baking industry and are considered "clean label." CGA esterases cleave CGA into caffeic and quinic and have been isolated from both fungal and bacterial sources. CGA esterases have been used for hydrolysis of hydroxycinnamic acid derivatives in coffee, wheat, and rapeseed. Notably, CGA cleavage by fungal esterases was evaluated by Zhang et. al. (2019) as a method to prevent greening in sunflower protein isolates. However, the study was inconclusive because isolates were kept under acidic conditions throughout the experiment, which lowers greening regardless of whether CGA is hydrolyzed or not.

While both fungal and bacterial esterases hydrolyze CGA, bacterial CGA esterases are considerably more active. Our group recently characterized a CGA esterase from *Lactobacillus helveticus* that has a $K_m$ of 0.090 mM and a $k_{cat}$ of 82 s$^-$ and was shown to be stable over a wide range of pH and temperatures (Example 1). We further demonstrated that *L. helveticus* CGA esterase (henceforth simply referred to as CGA esterase) rapidly hydrolyzed CGA in sunflower meal and fully eliminated greening in alkaline extracted protein isolates. These results represented the first time non-greening sunflower protein isolates could be produced under alkaline conditions without any prior processing steps such as dephenolization.

Since the CGA esterase was active in both defatted and undefatted sunflower meals and was shown to cleave CGA in both dilute solutions and sunflower meal suspensions, CGA esterase would be able to cleave CGA in both sunflower flour and butter.

EXAMPLES

Example 1. A Highly Active Esterase from *Lactobacillus helveticus* Hydrolyzes Chlorogenic Acid in Sunflower Meal to Prevent Chlorogenic Acid Induced Greening in Sunflower Protein Isolates

Materials and Methods

All reagents and HPLC consumables were purchased from Sigma Aldrich and Fisher Scientific. Lyric Wild Bird Food sunflower seeds were purchased from Home Depot.

Chlorogenic acid esterase cloning. The gene coding for CGA esterase was purchased from Genewiz (Cambridge, MA) and was codon-optimized for expression in *E. coli*. The CGA esterase gene was amplified using the following primers by PCR:

Forward:
```
                              (SEQ ID NO: 1)
5' GCCCGCTAGCATGAGCCGCATTACCATTGAACGC
```

Reverse:
```
                              (SEQ ID NO: 2)
5' CCGCGAGCTCTTAAAACGCCGGTTTCAGAAACTGCG
```

The forward and reverse primers have an NheI and Sac restriction enzyme site, respectively, and were inserted into a pET28a plasmid by restriction digest cloning.

Chlorogenic acid esterase purification and expression. CGA esterase was expressed in *E. coli* (BL21) in 2.8 L Erlenmeyer flasks containing 1.0 L LB (Miller) broth and 30 mg L$^{-1}$ kanamycin. Cells were grown for approximately 2-4 h at 37° C. in an orbital shaker set to 250 rpm until they reached an optical density (OD) at 600 nm of 0.6-1. Expression was induced by adding isopropyl-β-D-thiogalactopyranoside (IPTG) to a final concentration of 1.0 mM. The incubation temperature was then lowered to 18° C. and the expression continued overnight (16-20 h) with an orbital shaker speed of 200 rpm. Cells were then harvested by centrifugation at 5,000 rpm for 10 min and the pellet was transferred into Falcon tubes and centrifuged again at 5,000 rpm for 10 min. The supernatant was decanted and the pellet was stored at −20° C. until use.

Cells were lysed by microfluidization at 16,000 psi and the lysate was clarified by centrifugation at 12,500 rpm for 45 min at 4° C. The supernatant containing CGA esterase was loaded onto a Ni$^{2+}$ column pre-equilibrated with 50 mM Tris pH 8.0, 100 mM NaCl, and 20 mM imidazole. For elution of CGA esterase from the column, 50 mM Tris pH 8.0, 100 mM NaCl, 500 mM imidazole was applied using a linear gradient. SDS-PAGE was used to detect fractions containing CGA esterase and fractions containing the enzyme were pooled. This was followed by a two-step dialysis against a buffered solution containing 50 mM HEPES pH 8.0, 500 mM NaCl, and 10% glycerol. Each dialysis step proceeded for at least 6 h.

After dialysis, CGA esterase was concentrated using an Amicon stirred cell to approximately 10 mL and further concentrated in a 10 kDa centrifugal filter to approximately 5 mL. Purification was completed using an S200 gel filtration column pre-equilibrated with a buffered solution containing 50 mM HEPES pH 8.0, 500 mM NaCl, 10% glycerol. Fractions containing CGA esterase were detected using SDS-PAGE and pooled. Enzyme concentration was calculated using an extinction coefficient of 14,900 M$^{-1}$ cm$^{-1}$ at 280 nm.

Circular dichroism, dynamic light scattering and mass spectrometry. Circular dichroism (CD) spectra were taken on a Jasco J-1500 CD spectrophotometer. CGA esterase (0.2 mg mL$^{-1}$) was buffered in a solution of approximately 5 mM HEPES, pH 8.0. Spectra were recorded at 4° C. using the following settings: 100 nm min$^{-1}$ scan rate, 0.2 nm data pitch, 1.0 nm bandwidth, and 2 s integration time. Five acquisitions were averaged per experimental sample. To generate thermal denaturation curves, the CD signal at 222 nm was recorded as the temperature was gradually increased from 4° C. to 96° C. The T$_m$ was estimated by fitting a Boltzmann sigmoidal function to the denaturation curve. For CD spectra that were run at different pH, a concentrated CGA esterase stock solution was diluted to either 0.2 mg mL$^{-1}$ or 0.1 mg mL$^{-1}$ into solutions of 10 mM buffer at the pH indicated.

Dynamic light scattering (DLS) experiments were carried out using a Wyatt DynaPro Nanostar instrument set at 21° C.

Samples were prepared in twice-filtered 50 mM HEPES pH 8.0, 500 mM NaCl, 10% glycerol. Each CGA esterase measurement consisted of 10 scans with a 5 s acquisition time. The detector angle was set at 163.5° and the wavelength was equal to 532 nm.

The mass of CGA esterase was determined by MALDI-TOF mass spectrometry on intact protein using methods described previously (Medina et al., 2021).

Enzymatic assays to determine Michaelis-Menten parameters. Michaelis-Menten assays were conducted at 21° C. using an Agilent Technologies Cary 60 UV-Vis spectrophotometer. A stock solution of CGA was prepared by dissolving CGA in 50 mM HEPES pH 8.0 followed by calculation of concentration using the Lambert-Beer law with an extinction coefficient of 17,194 M$^{-1}$ cm$^{-1}$ at 330 nm. Subsequent dilutions of stock CGA were prepared to achieve final CGA concentrations of 0.02 mM, 0.04 mM, 0.06 mM, 0.10 mM, 0.20 mM, and 0.40 mM CGA. The final CGA esterase concentration in all enzymatic assays was 10 nM unless noted otherwise. All samples used for enzymatic assays were buffered in 50 mM HEPES, pH 8.0. Absorption scans were taken at 0.05 or 0.1 min intervals for 2 min between wavelengths of 250 nm and 400 nm. For CGA concentrations below 0.1 mM, the pathlength was 1 cm. Above 0.1 mM CGA, the pathlength was 0.5 cm.

To measure CGA depletion (Δ[CGA]), Equation 1 was used:

$$\Delta[CGA] = \frac{A - A_o}{\varepsilon_{CA} - \varepsilon_{CGA}} \qquad \text{(Equation 1)}$$

A is the absorbance at any time point in the reaction, A$_o$ is the initial absorbance, $\varepsilon_{CA}$ and $\varepsilon_{CGA}$ are the extinction coefficients at 340 nm of caffeic acid (CA) and CGA, which are 4.15 mM$^{-1}$ cm$^{-1}$ and 14.43 mM$^{-1}$ cm$^{-1}$, respectively. To generate initial rates, (Δ[CGA]| was plotted against time. The change in absorbance during the first minute of the reaction was fit to a linear curve, which is used to generate the reaction rate. We note that the rate of CGA depletion is equivalent to CA formation. To test the effect of salt on enzyme kinetics, the same procedure was used, except that the experiment was run with 0.04 mM CGA buffered in 50 mM HEPES pH 8.0 with 500 mM NaCl.

Temperature-dependence measurements. A circulating water bath was used to run enzymatic reactions at different temperatures to maintain the temperature in the spectrophotometer within 1° C. of the target temperature. Buffered solution, CGA, and CGA esterase samples were pre-incubated for 10 min at the desired temperature before starting a measurement. All other instrument parameters were the same as for room temperature measurements described above.

Sunflower meal and sunflower protein treatment with chlorogenic acid esterase. Sunflower seeds were ground using a KitchenAid coffee grinder in two 30 s increments and sieved through a 500 µm filter to make SFM. Two defatting methods were used: cold press and hexane extraction. To make cold pressed SFM, ground seeds were pressed in a Carver Hydraulic Unit Model 3912 3852-0 five times to a pressure of 9,000-10,000 psi. For hexane extracted SFM, fat was removed from ground seeds using a Soxhlet apparatus in 250 mL hexane for 18 h and subsequently dried using a Fischer Scientific Isotemp Oven Model 516G at 45° C. for 3 h. Cold pressed, hexane extracted, and undefatted SFM were then sieved through a 500 µm filter.

To make SPI, 12.5 g of cold pressed, hexane extracted, and undefatted SFM were buffered in 50 mM HEPES at pH 8.0. Samples were continuously stirred for about 10 min until all SFM was completely suspended. Then, 0.2 mg of CGA esterase per g of SFM was added. The final volume for all reactions was 125 mL. In untreated samples, a buffered solution of 50 mM HEPES, pH 8.0 was added instead of the enzyme solution. After 10 min, 0.1 M NaOH was added to each solution until pH reached 9.00±0.03. Samples were left to sit for 30 min and then centrifuged at 5,000 rpm for 20 min at 4° C. The supernatant was placed back into a 250 mL beaker and pH was lowered using 0.1 M HCl to reach an isoelectric pH of 5.00±0.03. Samples were allowed to precipitate at 4° C. overnight (14-16 h). The supernatant was discarded, and the precipitate was lyophilized for 20 h. All experiments (controls and CGA esterase treated samples) were duplicated.

Chlorogenic acid esterase activity in the sunflower meal supernatant and pellet. SFM (1 g) that was cold pressed, hexane extracted, or undefatted was buffered in 10 mL of 50 mM HEPES, pH 8.0. CGA esterase was added to a final concentration of 0.756 μM (0.02 mg mL$^{-1}$). Untreated samples received a solution of 50 mM HEPES, pH 8.0 instead of CGA esterase. Samples treated with CGA esterase were allowed to sit for 10 min and subsequently centrifuged at 10,000 rpm for 10 min. The supernatant was filtered through a 0.2 μm filter and loaded onto an HPLC while the pellet was lyophilized for 20 h. After lyophilization, 10 mL of 70% ethanol was then added to the dried pellet for 1 h to extract CGA. The pellet was subsequently centrifuged at 10,000 rpm for 10 min. The supernatant was then filtered through a 0.2 μm filter and loaded onto an HPLC.

Chlorogenic acid esterase kinetics in sunflower meal. To determine the Michaelis-Menten parameters of CGA esterase in undefatted SFM, SFM suspensions were made at following concentrations: 1.0 mg mL$^{-1}$, 2.5 mg mL$^{-1}$, 10.0 mg mL$^{-1}$, 30.0 mg mL$^{-1}$, and 100.0 mg mL$^{-1}$. All samples were made to a final volume of 10 mL in a solution containing 50 mM HEPES, pH 8.0. Treated samples contained a final enzyme concentration of 10 nM. Reactions were stopped by acidifying the solution by adding 120 μL of 37% HCl at regular intervals for 600 s. Samples were subsequently centrifuged at 10,000 rpm for 10 min. Control samples confirmed that stopping the reaction by acid quenching does not induce CGA hydrolysis. The supernatant was then filtered using a 0.2 μm filter and loaded onto an HPLC, as described above. The initial amount of CGA that was present prior to adding enzyme was measured using HPLC.

HPLC quantification of CGA and CA in sunflower meal and protein isolates. All solutions were diluted ten-fold in 0.1% formic acid in HPLC-grade water before analysis. Quantification of CGA and CA concentration was performed using an Agilent 1260 series HPLC instrument (Agilent Technologies) equipped with a quaternary pump, an automated sample injector, a diode array detector, and a 4.6 mm×150 mm Luna C18(2) column with a 5 μm particle size and 100 Å pore size (Phenomenex). The injection volume was 20 μL. To elute analytes, mobile phases composed of 0.1% formic acid in HPLC-grade water (A) and 0.1% formic acid in HPLC-grade acetonitrile (B) were used in a linear gradient. The gradient is as follows: 0 to 13% B in 1 min, up to 27% B at 8 min, up to 100% B at 8.5 min, isocratic at 100% B to 9.5 min, 100% B returned to 0% B at 9.6 min with 3 min post-time. The concentrations of CGA and CA were calculated from peak integration data based on 10-point standard curve that spanned a concentration range of 0 to 0.1 mg mL$^{-1}$.

Colorimetry of sunflower protein powders. A Hunter colorimeter (Konica Minolta, Inc. model: CM-2500D) was used to measure color changes in CIE L*a*b* in the protein powders after calibration using a white plate. Protein powders were put into glass containers and placed on a white background before taking measurements.

Results

Choice of Source Organism for the Chlorogenic Acid Esterase

Figure 2B:
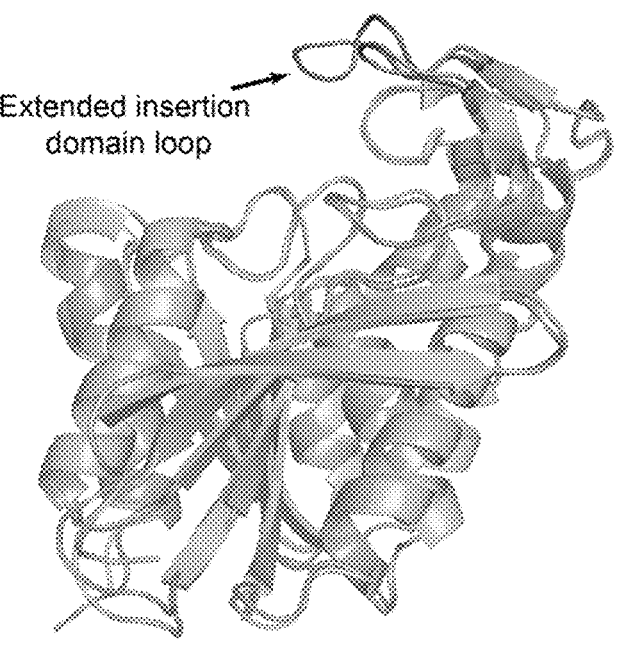
FIG. 2B: Structural alignment of *L. johnsonii* CGA esterase (PDB ID: 3PF8) with *L. helveticus* CGA esterase (8SKM). A single protomer of the dimer is depicted. The structures are very similar with a root mean square deviation (RMSD) value of 0.8 Å. The most important difference is a loop above the active site. In the *L. johnsonii* structure, the loop is a small beta hairpin whereas in *L. helveticus* CGA esterase, the loop is larger and extends above the active site cleft, as indicated by the arrow.

To date, putative CGA esterases have been found in only a small number of bacterial species, mostly among the genus *Lactobacillus*. The amino acid sequences of *Lactobacillus* CGA esterases are conserved (FIG. 2A) and their protein structures are predicted to be similar (FIG. 2B). In a comparative study, the activity of several CGA esterases was assessed by measuring the hydrolysis of the model substrate p-nitrophenyl acetate (Fritsch et al., 2017). This study revealed that hydrolysis activity was similar across CGA esterases, differing only about 50% between species. Because no CGA esterase exhibited higher activity than the rest, we focused on a CGA esterase with good thermostability. CGA esterase from *L. helveticus* was selected since it was reported to be both thermostable and among the more active CGA esterases.

Expression, Purification, and Physical Characterization of Chlorogenic Acid Esterase from *L. helveticus*

CGA esterase from *L. helveticus* (Genbank ID: WP_025283955.1, Uniprot ID: U6F2K7) was cloned into a pET28a expression plasmid, heterologously expressed in *Escherichia coli*, and purified in two steps by affinity and gel filtration chromatography. CGA esterase eluted in three peaks from the gel filtration column. The elution volume of the main peak indicated that the protein had a size of approximately 60 kDa, which is consistent with the expected dimeric state of CGA esterase. After the gel filtration step, there were no detectable impurities. The typical yield of purified CGA esterase after gel filtration was 20 mg of protein per liter of growth media.

Figures 3A, 3B, 3C, 3D, 3E:
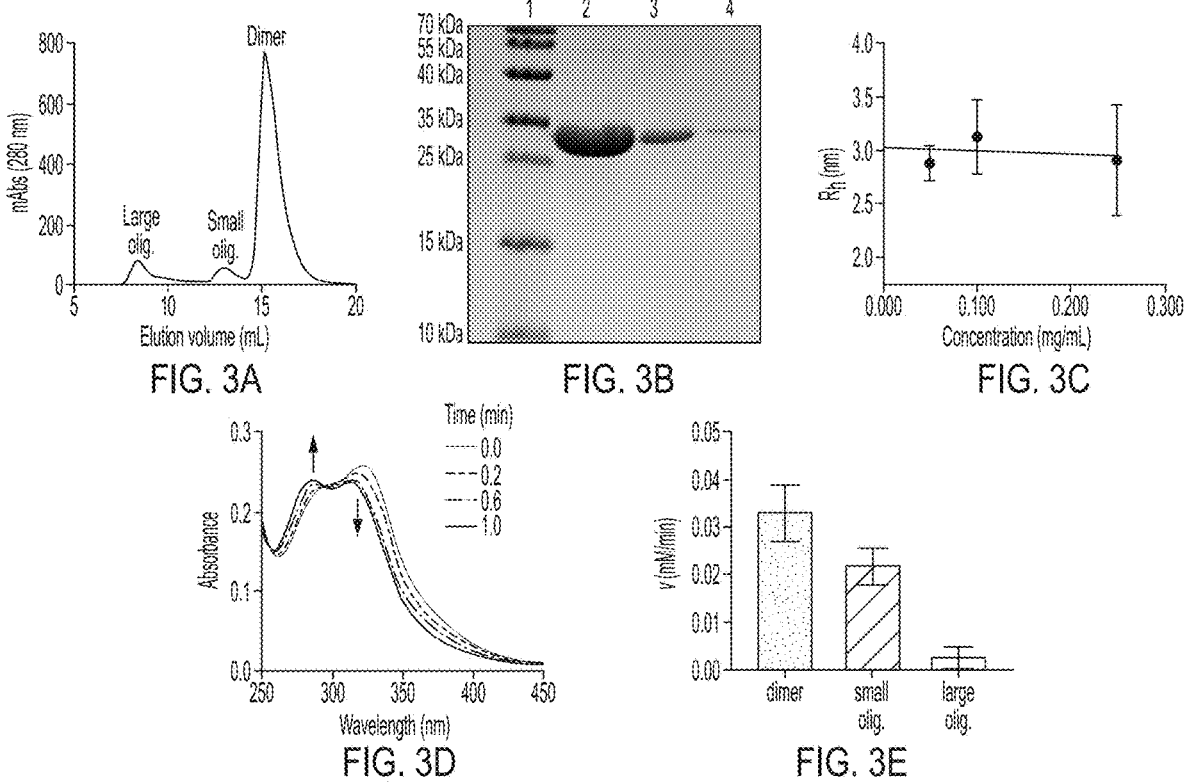
FIG. 3A: Gel filtration chromatogram of CGA esterase indicating that it elutes in three different aggregation states.
FIG. 3B: Sodium dodecyl-sulfate polyacrylamide gel electrophoresis (SDS-PAGE) of CGA esterase following gel filtration, where lane 1 is the protein ladder and lanes 2-4 contain 0.069 mg, 0.0069 mg, and 0.00069 mg of CGA esterase, respectively.
FIG. 3C: CGA esterase radius measured by DLS indicating that the concentration independent radius is 3.03 nm, consistent with a ca. 60 kDa protein.
FIG. 3D: Absorption spectra of the hydrolysis of 0.02 mM CGA by CGA esterase over time. Arrows indicate changes in absorbance relating to decreasing CGA and increasing CA concentrations.
FIG. 3E: Rate of 0.04 mM CGA breakdown by the CGA esterase in its three aggregation states, demonstrating that the dimer is the active form of the enzyme.

The oligomeric state of the main gel filtration peak was confirmed by DLS, which revealed a concentration independent radius of 3.03±0.2 nm (FIG. 3C). This corresponds to the expected radius of a 60 kDa globular protein. The two minor peaks correspond to a trimer or tetramer (henceforth referred to as small oligomer) and a large oligomer, respectively. Mass spectrometry confirmed that CGA esterase had the expected molecular mass of 30 kDa per protomer. In addition, mass spectrometry revealed partial gluconylation of the protein, a common N-terminal posttranslational modification of proteins that are recombinantly expressed in *E. coli*.

To determine the relative activity of the different oligomers, we analyzed the rates of CGA hydrolysis into caffeic and quinic acid by absorption spectroscopy (FIG. 3D). The dimer had the largest rate of CGA hydrolysis, indicating that it indeed represents the active form of the enzyme (FIG. 3E). The rate of hydrolysis of the small oligomer peak was about half of that of the dimer and the large oligomer was inactive. The secondary structures of the dimer, small and large oligomers of CGA esterase were analyzed by CD spectroscopy. CGA esterase is expected to consist of a mix of α-helices and β-sheets (FIG. 2B). While the spectrum of the dimer was consistent with a mixed α/β-domain protein, the signals of the oligomers were weaker, which indicates partial protein unfolding (FIG. 4A). Thus, the lower activity of oligomers was likely due to a loss in secondary structure. Since the oligomers represent only a minor component of the purified protein, they were not used for further experiments. Follow-up gel filtration experiments demonstrated that the dimeric enzyme does not aggregate after purification and stays stable at elevated temperatures for hours, meaning that CGA esterase will not lose activity over time by unfolding and/or oligomerizing.

Thermal and PH Stability of Chlorogenic Acid Esterase

We determined CGA esterase's structural stability by CD spectroscopy, which demonstrated that the protein is thermostable with a $T_m$ of 65° C. (FIG. 4B). Once denatured, the protein does not refold when cooled back to room temperature. CGA esterase was also stable over a range of pH, as CD spectra were identical between pH 6.0 and 9.0 (FIG. 4C).

Kinetic Characterization of Chlorogenic Acid Esterase

Figures 9A, 9B, 9C:
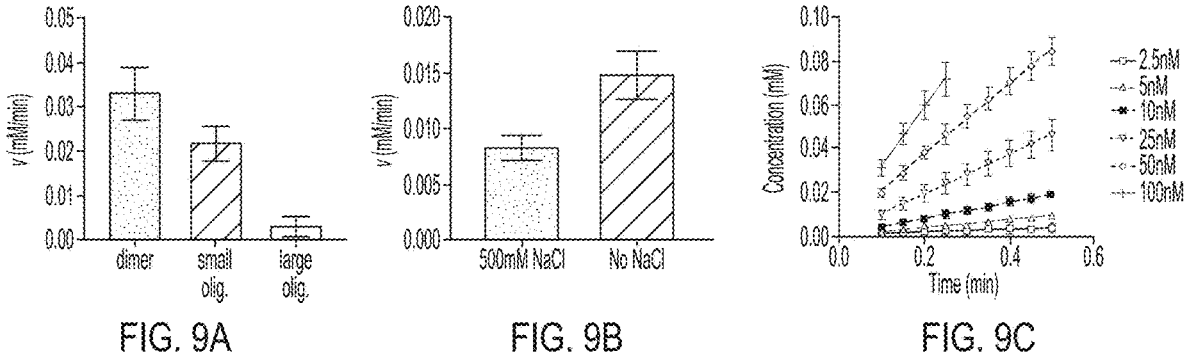
FIG. 9A: Rate of CGA hydrolysis using 10 nM CGA esterase and 0.04 mM CGA buffered in 50 mM HEPES or in 50 mM HEPES, 500 mM NaCl.
FIG. 9B: Caffeic acid (CA) concentration vs. time plot using 0.2 mM CGA and differing concentrations of CGA esterase. The slope generated from the concentration vs. time plot is the rate of CGA hydrolysis.
FIG. 9C: CGA hydrolysis scales linearly with enzyme concentration.

The extent to which buffer composition influences protein activity was determined since protein yields were highest when purification was carried out in a buffer containing 500 mM salt. As shown in FIG. 9A, reactions carried out in 50 mM HEPES, pH 8.0 had higher activity than in the purification buffer, suggesting that kinetic experiments could be carried out in absence of salt. We next determined that no CGA hydrolysis occurred without enzyme and that the rate of CGA hydrolysis was directly proportional to the amount of enzyme (FIGS. 9B and C). This indicates that all CGA hydrolysis was entirely an effect of enzymatic catalysis.

Figure 5:
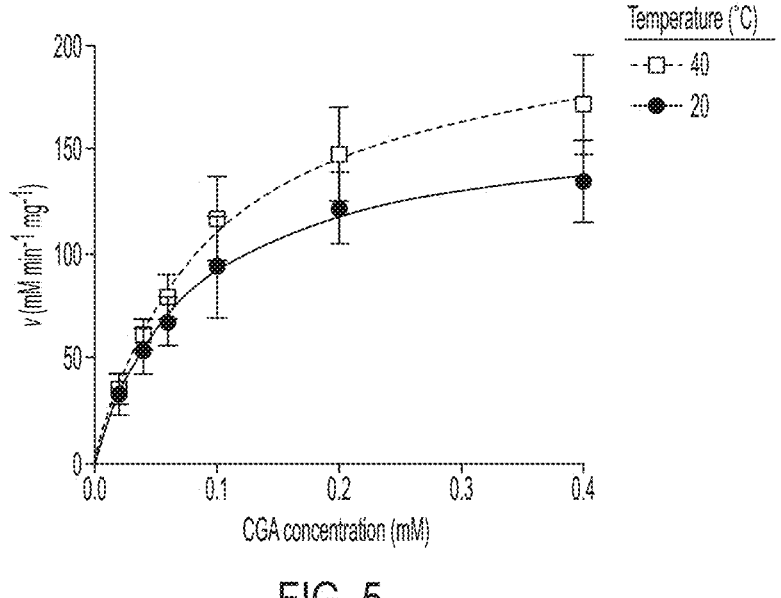
FIG. 5: Michaelis-Menten analysis of CGA esterase at 20° C. and 40° C. Data is based on four independent triplicate averages. At 20° C., $K_m$ is 0.090±0.038 mM, $V_{max}$ is 170.2±32.3 mM min$^{-1}$ mg$^{-1}$. At 40° C., $K_m$=0.096±0.006 mM and $V_{max}$ is 215.4±31.7 mM min$^{-1}$ mg$^{-1}$.
Figure 10A:
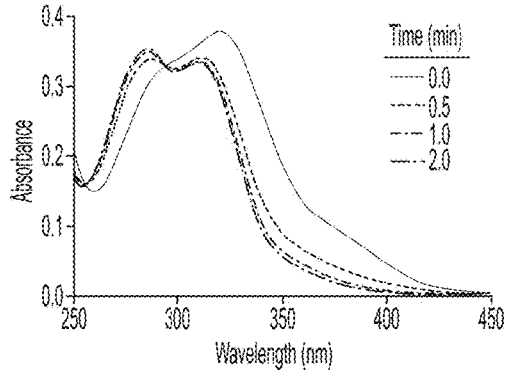
FIG. 10A: Absorption spectra of the hydrolysis of 0.02 mM CGA by CGA esterase over a 2 min time span
Figure 10B:
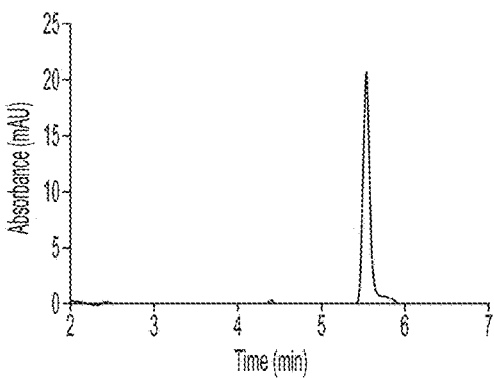
FIG. 10B: representative HPLC chromatogram of the same reaction. Both methods indicate CGA hydrolysis is complete, demonstrating that absorption spectroscopy can accurately determine the extent of CGA hydrolysis.
Figures 11A, 11B:
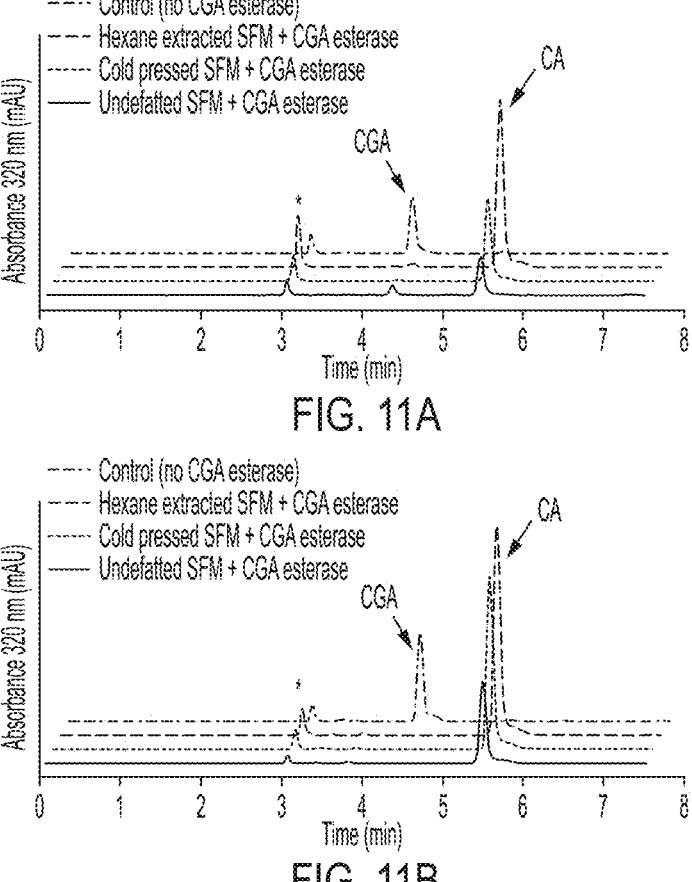
FIG. 11B: Structure of CGA esterase from *Lactobacillus helveticus* (PDB ID 8SKM).

The Michaelis-Menten parameters for CGA esterases are shown in FIG. 5 and Table 1. The Km is 0.090±0.038 mM, Vmax is 170.2±32.3 mM min−1 mg−1, and kcat is 82±15.6 s−1. The Km is comparable to reported values for CGA binding to *L. johnsonii* CGA esterase and the previously reported value for *L. helveticus* CGA esterase (Lai et al., 2009; Song & Baik, 2017). However, Vmax is 300-fold higher than previously reported (Song & Baik, 2017). The measurements represent independent averages from CGA esterase that were generated from multiple different growths and purifications. Furthermore, the accuracy of the absorbance-based CGA hydrolysis assays was confirmed using an HPLC-based measurement (FIG. 10). We are therefore confident that the unexpectedly high Vmax is accurate.

TABLE 1

Comparison of enzyme kinetics values for CGA esterases from fungal and bacterial sources toward the substrate CGA.

| Source | $K_m$ (mM) | $V_{max}$ (mM min−1mg−1) | Citation |
|---|---|---|---|
| *A. niger* | 0.002 | 0.0228 | Zhang et. al., 2019 |
| *A. niger* | 0.007 | 0.0150 | Benoit et al., 2007 |

12

TABLE 1-continued

Comparison of enzyme kinetics values for CGA esterases from fungal and bacterial sources toward the substrate CGA.

| Source | $K_m$ (mM) | $V_{max}$ (mM min−1mg−1) | Citation |
|---|---|---|---|
| *L. johnsonii* | 0.053 | n/a | Lai et al., 2009 |
| *L. helveticus* | 0.153 | 0.5596 | Song & Baik, 2017 |
| *L. helveticus* | 0.090 | 170.2 | This study |

Since enzyme activity is often temperature-dependent, we determined to what extent CGA esterase activity changes with temperature. CGA esterase activity increases only weakly at elevated temperatures, as shown in FIG. 5. The Michaelis-Menten parameters at room temperature and 40° C. are very similar (FIG. 5). Further measurements of the rate of CGA hydrolysis in 10° C. temperature increments between 20° C. and 50° C. confirmed that enzymatic activity only increases slightly with elevated temperatures. The small temperature-dependence of *L. helveticus* CGA esterase is similar to that of CGA esterases from the bacteria *L. gasseri* and *Bif. animalis* with the model substrate p-nitrophenyl acetate, which had a very weak temperature-dependence between 20° C. and 40° C. (Fritsch, C., Jansch, A., Ehrmann, M. A., Toelstede, S., & Vogel, R. F. (2017). Characterization of Cinnamoyl Esterases from Different Lactobacilli and Bifidobacteria. *Curr Microbiol,* 74 (2), 247-256.

Enzymatic CGA Hydrolysis in Sunflower Meal

After demonstrating the effectiveness of CGA esterase at cleaving CGA, we tested if the enzyme could hydrolyze CGA in SFM. Sunflower seeds have a high lipid content of about 50-60% w/w. Since CGA esterase has structural similarity to monoglyceride lipases, we were concerned that lipids interfere with CGA binding to the enzyme. We, therefore, compared the enzyme's performance in seeds that were undefatted to those that were defatted using two different methods: cold pressing and hexane extraction.

Figures 6A, 6B, 6C, 6D:
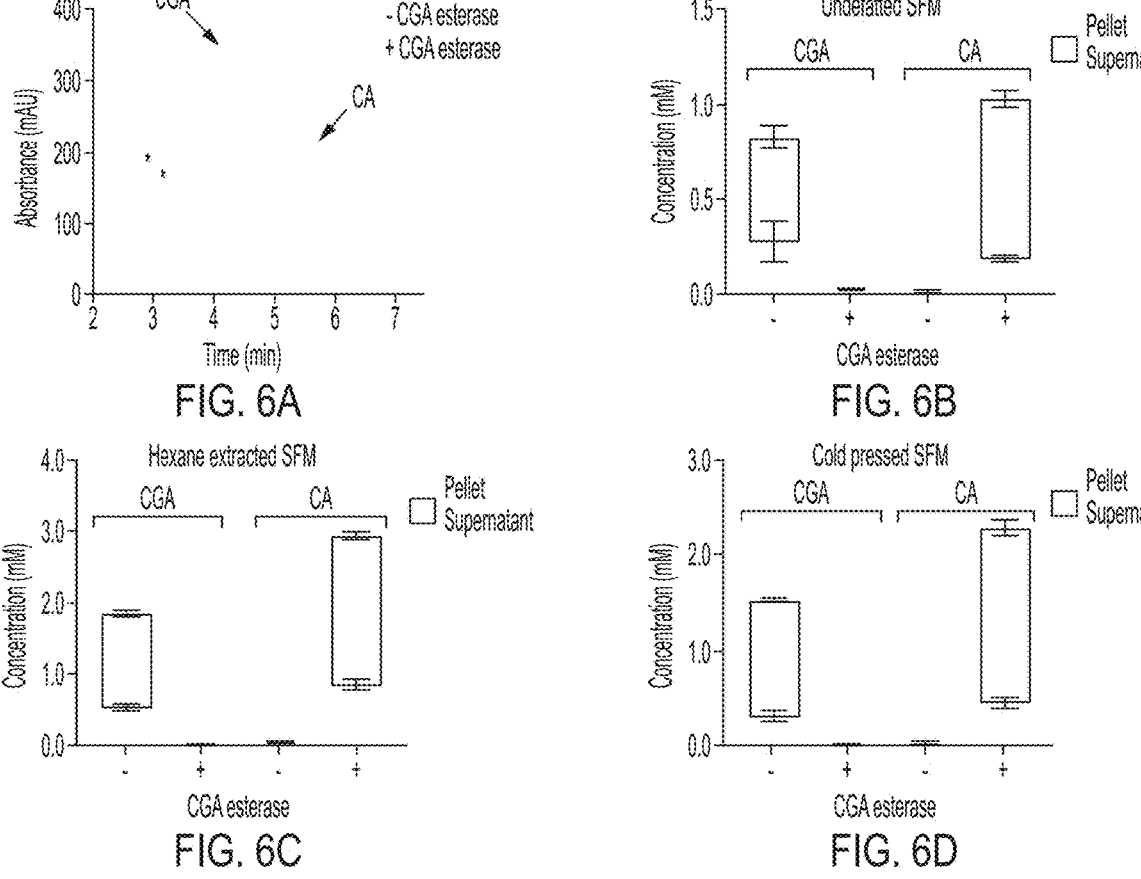
FIG. 6A: Representative high performance liquid chromatography (HPLC) chromatograms from sunflower meal (SFM) treated with CGA esterase (+) and untreated SFM (−). CGA and CA were detected at 320 nm. The retention times of CGA and CA are 4.3 min and 5.4 min, respectively. Peaks marked with an asterisk are other compounds found in the meal that are neither CGA nor CA.
FIG. 6B: Bar graph comparing CGA hydrolysis (formation of CA and depletion of CGA) in the pellet and supernatant in undefatted SFM.
FIG. 6C: hexane extracted SFM.
FIG. 6D: cold pressed SFM. CGA breakdown is essentially complete in all three conditions.

CGA hydrolysis in the meal was initiated by adding CGA esterase to SFM that was suspended in a buffered solution. To determine whether hydrolysis was taking place in both CGA that diffused into the aqueous phase and CGA that remained stuck in the suspended meal particles, CGA hydrolysis was measured for both. As shown in FIG. 6, 11, and Table 2, CGA esterase rapidly cleaved CGA in each of the three different types of samples, regardless of lipid content. Cleavage was complete (>99%) in defatted samples and ca. 96% complete in undefatted samples. Furthermore, CGA was hydrolyzed in both the aqueous solution and suspended meal. Additional experiments described in Example 2 demonstrate that CGA esterase also hydrolyzes CGA when the meal is nearly dry.

TABLE 2

Chlorogenic and caffeic acid content in the pellet and supernatant of CGA esterase treated and untreated sunflower meal powders.

| Lipid extraction technique | CGA esterase | Pellet | | Supernatant | |
|---|---|---|---|---|---|
| | | mg CGA/g meal | mg CA/g meal | mg CGA/g meal | mg CA/g meal |
| Undefatted | − | 0.99 ± 0.38 | 0.03 ± 0.00 | 1.96 ± 0.19 | 0.02 ± 0.00 |
| | + | 0.11 ± 0.01 | 0.34 ± 0.03 | 0.00 ± 0.00 | 1.52 ± 0.08 |
| Hexane extracted | − | 1.94 ± 0.16 | 0.06 ± 0.00 | 4.64 ± 0.16 | 0.04 ± 0.00 |
| | + | 0.03 ± 0.00 | 1.55 ± 0.14 | 0.00 ± 0.00 | 3.77 ± 0.10 |
| Cold pressed | − | 1.10 ± 0.22 | 0.04 ± 0.01 | 4.33 ± 0.06 | 0.03 ± 0.00 |
| | + | 0.02 ± 0.00 | 0.81 ± 0.11 | 0.00 ± 0.00 | 3.33 ± 0.15 |

− means that no enzyme and + means that enzyme is present.

Kinetics of CGA Hydrolysis in Sunflower Meal

Figure 7:
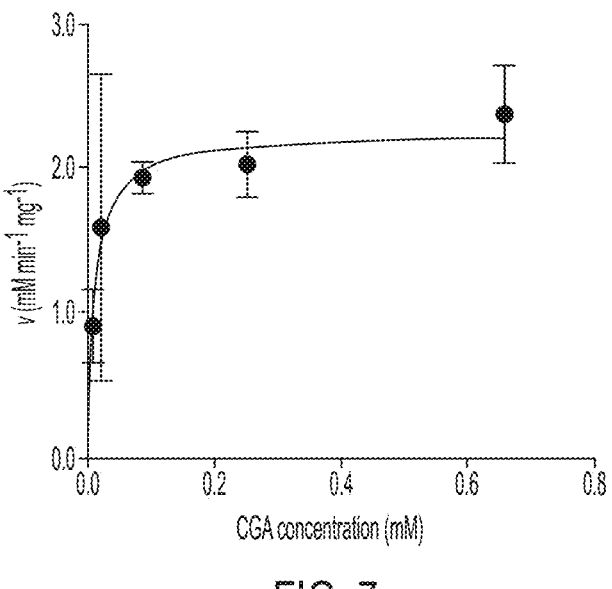
FIG. 7: Michaelis-Menten data for CGA esterase kinetics in SFM supernatant at pH 8.0 and 20° C. Averaged data is processed from a minimum of three replicates. The $K_m=0.020$ mM (95% CI=0.003 mM to 0.03 mM) and $V_{max}=2.716$ mM min$^{-1}$ mg$^{-1}$ (95% CI=1.805 mM min$^{-1}$ mg$^{-1}$ to 2.746 mM min$^{-1}$ mg$^{-1}$).

We next were interested in determining to what extent the kinetics of CGA hydrolysis in SFM differed from the kinetics with pure CGA in buffer. To do so, the concentration of SFM, and thus of CGA, was varied to obtain the enzyme's $K_m$ and $V_{max}$ when operating in the meal. As shown in FIG. 7, enzyme activity increased hyperbolically with meal concentration, as expected. The $K_m$ and $V_{max}$, listed in FIG. 7, were both lower than in buffered solution. Overall, the kinetics data indicates that maximal CGA hydrolysis activity is achieved when the concentration of the meal is approximately 100 mg $mL^{-1}$.

Production of Sunflower Protein from Enzymatically Treated Meal

After demonstrating that CGA esterase hydrolyzes CGA in SFM, we investigated if enzymatic treatment improves the color properties of SFM-derived protein isolates. Protein isolates were produced from meal using alkaline extraction since this method provides higher protein yield compared to acidic extraction and is more widely used in isolating plant protein. Experiments were run with undefatted meal, and defatted meal that was either cold pressed or hexane extracted. CGA hydrolysis was complete in samples that were treated with CGA esterase, whereas CGA was present in samples that did not receive enzyme (Table 3).

TABLE 3

Total CGA and CA content in treated and untreated samples of sunflower protein isolates.

| Lipid extraction technique | CGA esterase | mg CGA/g protein | mg CA/g protein |
|---|---|---|---|
| Undefatted | – | 2.60 ± 0.17 | 0.08 ± 0.07 |
|  | + | 0.00 ± 0.00 | 1.11 ± 0.38 |
| Hexane extracted | – | 3.90 ± 0.81 | 0.70 ± 0.19 |
|  | + | 0.00 ± 0.00 | 3.38 ± 0.25 |
| Cold pressed | – | 4.23 ± 0.25 | 0.20 ± 0.04 |
|  | + | 0.00 ± 0.00 | 3.62 ± 0.05 |

– means that no enzyme and + means that enzyme is present.

Figure 8:
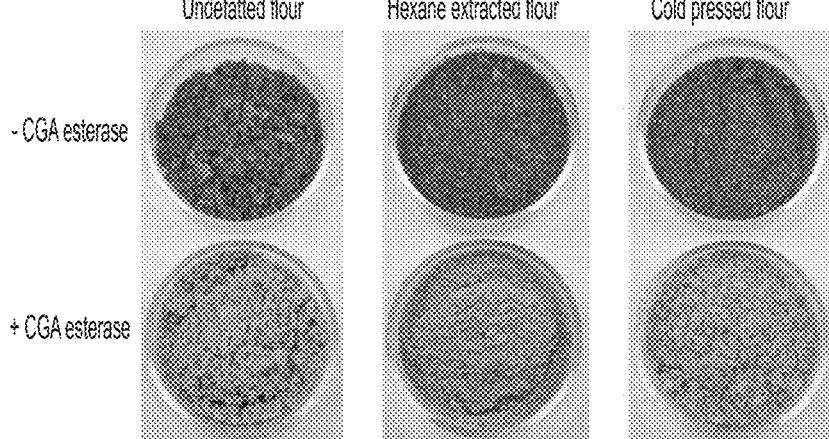
FIG. 8: Protein isolates made from treating three types of SFM.

Finally, we determined that CGA esterase improves the color of SPI. As shown in FIG. 8, all untreated protein isolates displayed a characteristic deep green color, regardless of fat content. In stark contrast, all enzymatically treated samples were colored a pale shade of brown. CIE L*a*b* analysis results, shown in Table 4, indicate the enzymatic treatment significantly lowered the greening index (more positive value for a*) and increased lightness (higher L* value). Although all treatments provided complete greening prevention, there was a slight difference in color between the protein isolates that were cold pressed and solvent extracted. The color difference is in the brown range of the spectrum and likely due to Maillard reactions or phenol oxidation. Taken together, our data strongly suggests that enzymatic treatment of SFM completely prevents greening during alkaline protein isolation.

TABLE 4

L*a*b* values of protein isolates made from treatment of undefatted and defatted (hexane extracted and cold pressed) samples treated with CGA esterase.

| Fat extraction technique | CGA esterase | L* | a* | b* |
|---|---|---|---|---|
| Undefatted | – | 24.31 ± 4.19 | −7.88 ± 0.43 | 2.99 ± 0.14 |
|  | + | 43.05 ± 5.02 | 1.18 ± 1.02 | 8.14 ± 0.96 |

TABLE 4-continued

L*a*b* values of protein isolates made from treatment of undefatted and defatted (hexane extracted and cold pressed) samples treated with CGA esterase.

| Fat extraction technique | CGA esterase | L* | a* | b* |
|---|---|---|---|---|
| Hexane extracted | – | 35.02 ± 8.97 | −4.57 ± 2.20 | 2.02 ± 2.34 |
|  | + | 34.28 ± 3.00 | −0.48 ± 0.21 | 6.70 ± 2.17 |
| Cold pressed | – | 24.61 ± 0.91 | −7.87 ± 0.45 | 3.55 ± 0.21 |
|  | + | 39.86 ± 9.48 | −0.61 ± 0.21 | 6.11 ± 2.67 |

– means that no enzyme and + means that enzyme is present.

Discussion

Here, we characterized a thermostable CGA esterase from *L. helveticus* that was very active against CGA and completely hydrolyzed CGA in SFM. We further showed that CGA esterase treatment of SFM allows the production of SPI that are pale brown in color instead of green.

Prior to this work, there had been several reports on the biochemical and structural properties of bacterial CGA esterases (Fritsch et al., 2017; Lai et al., 2009; Song & Baik, 2017; Wang et al., 2004). Our biochemical characterization of *L. helveticus* CGA esterase largely agrees with previous work. The protein's secondary structure, thermostability, and the Km towards CGA are similar to those of other *Lactobacillus* CGA esterases. There are, however, some key areas where our results differ from previous reports. We purified *L. helveticus* CGA esterase as a dimer. This agrees with the oligomeric state found in the *L. johnsonii* CGA esterase crystal structure (Lai et al., 2011), but not with a previous report on *L. helveticus* CGA esterase that stated the enzyme was a monomer (Song & Baik, 2017). There is a large surface area between protomers in the CGA esterase crystal structure, which is consistent with our data that indicate the dimer remains stable over time and over a wide concentration range (FIG. 3). Together with our results that demonstrate that higher oligomeric states of CGA esterase are less active (FIG. 3), we conclude that the dimer is the native and functional form of the enzyme.

We did not observe a strong temperature dependence of the activity for CGA esterase between 20° C. and 50° C., which makes *L. helveticus* CGA esterase similar to *Bif animalis* and *L. gasseri* CGA esterase, but different from other *Lactobacillus* CGA esterases. Thus, the temperature-dependence of the CGA hydrolysis reaction appears to differ based on the bacterial origin of the enzyme. The structural and mechanistic basis for this difference is unclear since bacterial CGA esterases are similar in terms of amino acid sequence and predicted structure.

The most significant difference between our work and previous reports is the unexpectedly high Vmax. The reason for the large Vmax is unclear. That said, *L. helveticus* CGA esterase's kcat of 82 s-1 lies within the reported range of structurally related α/β hydrolases such as hormone-sensitive lipase family carboxylesterases (Chahinian et al., 2005) and bile salt hydrolases (Kumar et al., 2006) that cleave substrates that are similar in size to CGA. When compared to fungal CGA esterases, *L. helveticus* CGA esterase offers advantages. First, it is much more active. Fungal esterases from *A. niger* have a $K_m$ in the low µM range and a $V_{max}$ of 0.02 mM $min^{-1}$ mg-1, which is approximately 8,500-times lower than *L. helveticus* CGA esterase. Since CGA hydrolysis in SFM is not limited by substrate binding, the higher $V_{max}$ for the bacterial enzyme suggests it will be more effective at hydrolyzing CGA. Second, *L. helveticus* CGA esterase maintains better thermostability than its fungal counterparts. *A. niger* CGA esterase is rapidly inactivated at temperatures above 40° C., whereas the *L. helveticus* enzyme remains fully folded at 40° C. over time and active until at least 50° C. Third, the yield of recombinantly expressed *L. helveticus* CGA esterase is approximately 20 mg of protein per L of growth medium which far exceeds that of *A. niger* CGA esterase, which is produced in the native host with yields of <1 mg $L^{-1}$ of growth medium.

After characterizing the biochemical properties of *L. helveticus* CGA esterase, we determined that it cleaved CGA in SFM very effectively, achieving close to 100% conversion of CGA into caffeic and quinic acid in 10 min. CGA esterase hydrolyzes CGA in aqueous solution and CGA that remains trapped within the meal (FIG. 6). To the best of our knowledge, this observation is the first instance that CGA esterase activity was directly demonstrated in both aqueous and solid media. Furthermore, CGA esterase hydrolyzes CGA to near completion in undefatted meal. This suggests that lipids do not significantly inhibit CGA esterase.

The kinetics of CGA hydrolysis in SFM differ from that in buffer alone. The apparent Michaelis-Menten parameters, $K_m$ and $V_{max}$, were 0.020 mM and 2.716 mM $min^{-1}$ $mg^{-1}$, respectively, indicating a 4.5-fold lower $K_m$ and 60-fold lower $V_{max}$ compared to CGA in a simple buffered solution. Kinetic analysis of enzymes in complex food mixtures is rarely done. The decline in $K_m$ and $V_{max}$ is characteristic of an uncompetitive inhibition process. Sunflower seeds are known to contain potent peptide inhibitors that act on trypsin proteases. Since trypsin proteases have a similar active site and mechanism as CGA esterases, peptide inhibitors may lower CGA esterase activity in the meal.

Despite its lower enzymatic activity in meal compared to buffered solution, CGA esterase is still effective at removing CGA in SFM. Its in situ activity is similar to lipases and xylanases, two hydrolases that are used in commercial breadmaking. CGA esterase was used at a concentration of 200 ppm (0.2 mg of enzyme per gram of SFM) to break down CGA in meal. This level is equivalent to a xylanase used at 200 ppm and similar to widely used lipases, such as Palatase 20,000, which are used at 100-300 ppm. To demonstrate a potential application of CGA esterase, we produced pale brown SPI that were generated through an alkaline extraction process (FIG. 8). The method represents an improvement over existing methods of making SPI since it allows SPI to be made using the standard, high-yielding alkali process that is used for other seed-derived protein isolates without the need to de-phenolize SFM first. We expect that making protein isolates from sunflower meal that is left over as a byproduct of sunflower oil pressing will be particularly useful. The meal is currently considered a low-value product that is either discarded or used as animal fodder. CGA esterase treatment will make the conversion of SFM into protein powders economically appealing by providing a process to make affordable and nutritious sunflower seed-derived protein powders.

Example 2. Preventing Chlorogenic Acid Quinone-Induced Greening in Sunflower Cookies by Chlorogenic Acid Esterase Materials. Sunflower kernels (Lyric Wild Bird Food) were obtained from Home Depot. CGA esterase was purified as described in Example 1. For all experiments, CGA esterase was buffered in 50 mM HEPES, pH 8.0, unless otherwise specified. All buffers utilized for experiments were comprised of 50 mM HEPES, pH 8.0. All-purpose flour (UPC: 016000106109) (First Street), sunflower seed butter (Once Again unsweetened and salt-free, UPC 044082530413), fresh eggs, baking soda (UPC: 033200016700), vanilla extract (UPC: 089836185327), salt (UPC: 041512005275), and maple syrup (UPC: 681170411201) were purchased from local grocery stores. All solvents and acids were analytical or HPLC grade (Fisher Scientific).

Cookie formulations and baking conditions. The cookie dough formulation consisted of baking soda (2.2 g), salt (2.2 g), whole egg (46.8 g), maple syrup (76.3 g), vanilla extract (2.2 g), flour (145.8 g), and butter (87.5 g). CGA esterase treatments in SFF, utilized almond butter instead of SFB. The wet (sunflower or almond butter, maple syrup, eggs, and vanilla extract) and dry (flour, baking soda, and salt) ingredients were mixed separately and subsequently combined and mixed for 75 s with an electric hand mixer. The dough was rolled out and cut to the following dimensions: 6 mm thickness and 40 mm diameter. Cookies were baked for 7 min in a convection oven preheated to 149° C. (300° F.) and allowed to cool at room temperature for 10 min before further analysis.

Preparation of sunflower butter cookies with chlorogenic acid/CGA esterase. Two concentrations of CGA esterase, $1.72 \times 10^{-1}$ mg and $1.72 \times 10^{-2}$ mg of enzyme per gram of sunflower butter, were added to 97.48 g of sunflower butter. The volume of the enzyme was <3 mL. Control cookies were made by adding buffer instead of enzyme solution. The mixture was allowed to stand for 10 min and stirred for 1 min after 3 min and 7 min. Cookies were then prepared as described above.

Preparation of sunflower flour cookies with CGA esterase. Sunflower flour was made by grinding sunflower seeds in a coffee grinder for 1 min and sieved through a 500 μm steel mesh. CGA esterase treatment of the flour occurred in two ways: pretreatment and direct treatment. For pretreated flour, flour was suspended in 50 mM HEPES buffer at pH 8.0 before the addition of 0.09 mg CGA esterase per g of meal for 10 min. Following enzymatic treatment, sunflower flour was then lyophilized for 20 h. The resulting flour was added to make cookies as described above. For the direct treatment, sunflower seed flour was prepared similarly in 50 mM HEPES buffer at pH 8.0 and lyophilized without the addition of the enzyme. The esterase (0.09 mg/g) was then added directly to the lyophilized sunflower flour during cookie dough preparation, as described above.

Cookie diameter, height, and spread ratio measurement. The average diameter and height (mm) of sunflower cookies were measured using a digital caliper. The spread ratio was then calculated as the ratio of the average diameter to the average height.

Moisture content and fat extraction. After baking, moisture and crude fat content of the cookies were determined using AOAC Official Methods 934.06 and 948.22, respectively (AOAC 2006). To determine the moisture content, approximately 5 g of the cookie samples were dried in a vacuum oven (Model 3618-5, Thermo Scientific) for 24 h at 70° C. at a pressure of 25 bar. Crude fat content was determined by Soxhlet extracting 4-5 g of the dried cookies samples for 16-24 h in hexane.

High-performance liquid chromatography (HPLC) quantification of phenolic content in sunflower cookies. Following Soxhlet fat extraction, 0.5 g samples of the defatted sunflower cookies were placed into 10 ml of 70% ethanol to extract phenolics for HPLC analysis. The extraction mixture was vortexed and allowed to stand for 1 h before centrifuging at 17,000×g for 15 min (accuSpin Micro 17 R, Fisher Scientific). The extract was filtered through 0.20 µm syringe filters and analyzed with an Agilent 1260 Infinity II system (Agilent Technologies) equipped with a quaternary pump (G7111B), vial sampler (G7129A), and diode array detector (HS G7117C). The chromatographic separation was done through a Phenomenex Luna 5 µm C18(2) 100 Å LC column (150×4.6 mm) without controlling temperature. The samples were eluted using 0.1% formic acid in HPLC grade water (solvent A) and 0.1% formic acid in acetonitrile (solvent B) as specified in Example 1. The separation was done at a flow rate of 1.5 ml min$^{-1}$ by increasing the gradient of solvent B from 13 to 23% in 6 min. CGA and caffeic acid concentrations were detected at 320 nm and quantified using a standard curve between 0.00-0.10 mg ml$^{-1}$ CGA (y=172287x, $R^2$=0.994) and caffeic acid (y=248557x, $R^2$=0.967).

CIE L*a*b* determination of greening and browning. The color development in the cookies following baking was determined after 0, 1, 3, and 24 h. At each time point, replicate cookies were cut in half along the diameter. Color was determined as CIE L*a*b* values using a CM-2500D spectrophotometer (Konica Minolta, Inc.). The CIE L* values indicated lightness of the cookie (White=100; Black=0), a* values indicated greening (positive=red; negative=green), and b*values indicated yellowness (positive=yellow; negative=blue). Browning index was determined using Equation 2:

$$\text{Browning index} = \frac{(x - 0.31)}{0.172} \times 100. \quad \text{(Equation 2)}$$

where $$x = \frac{(a + 1.75L)a}{(5.645L + a - 3.013b)}$$

Water activity and cookie pH measurement. Water activity (aw) was determined on the cookie samples using a Series 3 Aqua Lab water activity meter after 0, 1, 3, and 24 h following baking.

Cookie samples (0.5 g) were mixed in 5 mL of nanopure water and homogenized for 1 min at 15,000×g (Multi-prep Homogenizer, ProScientific). The homogenized samples were incubated for 24 h at room temperature and centrifuged at 4,646×g for 30 min before measuring the pH of the supernatant (LabQuest 2 pH meter, Vernier Software & Technology).

Folin-Ciocalteu reducing capacity. The Folin-Ciocalteu reducing capacity in cookies treated with CGA esterase was determined after 1, 3, and 24 h following baking as described by (Singleton, R., & Rossi, 1965). One gram cookie samples were homogenized in nanopure water and centrifuged at 4,646×g for 30 min. A 100 µL supernatant was diluted to 3 ml with water and mixed with 0.5 ml of Folin-Ciocalteu reagent. After 5 min, 2 ml of 20% sodium carbonate was added, and the contents were vortexed and incubated at room temperature for 40 min. Absorbance was measured at 760 nm using CGA as a standard. The results were expressed as mg CGA/g of fresh weight material and analyzed by ANOVA with a significance level of P<0.05.

Statistical Analysis. Cookie spread ratio, moisture, and lipid content between treated and untreated cookies were analyzed by analysis of variance (ANOVA) at the initial time point after baking. For each treatment type, the differences in greening (a*) between treated and their corresponding untreated control over time (0, 1, 3, and 24 h) were analyzed by analysis of covariance (ANCOVA) to control for the known effects of pH and water activity, which were considered covariates, on greening. Statistical significance was determined at P<0.05. Tukey's HSD test was used to distinguish between significant groups where appropriate. Statistical analyses were performed using R statistical software v. 4.1.2 (R, 2021). All measurements were expressed as the mean±standard deviation of independent duplicate determinations.

Results and Discussion

Proximate analysis: Cookie samples were dried in a vacuum oven for 24 hr at 70° C. at a pressure of 25 bar. Moisture and crude fat extraction were determined as described in Pepra-Ameyaw et al. (2022). Samples (2±0.5 g) were dry ashed in pre-dried porcelain crucibles for 6 hr at 600° C. in a Thermo Scientific Lindberg/Blue M Moldatherm Box Furnace (AOAC 923.03-1923). Nitrogen content was determined by Kjeltec™ 8100 Foss apparatus, and crude protein was calculated using a nitrogen factor of 6.25 noted in AOCS method Ai 4-91(AOCS 2017).

Water activity, color, and texture analysis: Water activity was determined, as outlined by Pepra-Ameyaw et al. (2022). The internal colors of non-treated and esterase-treated cookies were measured at room temperature 24 hr post-baking. White tiles were used for calibration before color measurement. The color (CIE L*a*b* values) was determined using a CM-2500D spectrophotometer (Konica Minolta, Inc. Tokyo, Japan) by averaging the color of three cookies per treatment.

A compression force test was conducted on the SFF cookies using a Stable Micro Systems Texture Analyzer (Model Plus Upgrade) with a trigger force of 15 g and a load cell of 50 kg. The following parameters: 0.5 mm/s pre-, test and post-test speed, and 3 mm target value as stated by AMETEK Brookfield, Inc (Brookfield 2019) were used. The texture analyzer cycle speed of 0.5 mm/s, distance of 3 mm using a 2 mm diameter cylinder stainless probe were used. The average force was calculated using three cookies per treatment with four pseudoreplicate measurements per cookie.

High-performance liquid chromatography and ATR-FTIR spectroscopy: High-performance liquid chromatography was conducted as outlined by Pepra-Ameyaw et al. (2022) with no modifications. ATR-FTIR spectroscopy was performed as described by Ishii et al., (2021) with no modifications using dehydrated-defatted sunflower flour cookies that were finely ground with a mortar and pestle and passed through a 500-µm sieve.

Sensory study design: The study was reviewed and approved by Chapman University Institutional Review Board. Panelists from Chapman University and the local community were recruited through flyers, word of mouth, and in courses. Before participating in the study, informed consent was obtained from each subject. Participants were excluded if they had any food sensitivities (allergies or intolerances) and were not screened for regular cookie consumption. A total of 153 panelists participated in this study, of whom 39.2% were male, 59.5% were female and 1.3% were nonbinary. The age interval of panelists ranged from 18 to 64 years old, with 85.6% of participants aged 18-22, 5.9% were 23-29 years old, and 8.5% were 30 years old and above.

Surveys used for sensory evaluation: The RedJade platform (https://redjade.net/) was utilized to electronically provide the questionnaire for all sensory evaluation tests, with each panelist having access to a computer at their designated station. At the beginning of the sensory evaluation test, panelists were shown the concept card (FIG. 17) with characteristics of SFF and the nutritional label for the SFF cookie they would be consuming. Panelists were asked to indicate their acceptance of an SFF cookie based on the information on the concept card using a five-point scale from 1 ("would definitely not buy") to 5 ("definitely would buy").

Figure 18:
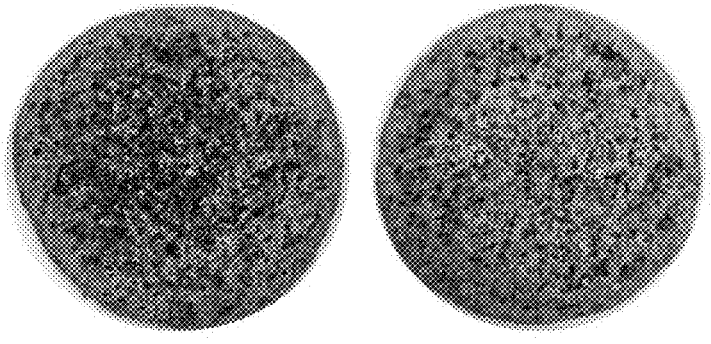
FIG. 18: Sunflower flour/SFF and sunflower flour cookies with (right) and without (left) esterase enzyme.

A tetrad difference test, a hedonic rating test, and purchasing intent were used to evaluate treated and non-treated SFF cookies. For the tetrad difference test, the panelists were provided with four coded samples of cookies and were asked to group the cookies into two groups, placing two cookies in each group based on their evaluation of similarity between the cookies (Ennis, 2012). The panelists were not instructed in the questionnaire to consume the cookies to differentiate them. For the acceptance test, panelists were asked to evaluate the cookies' texture, smell, flavor, and overall acceptability using 9-point hedonic scale survey questions, where 1=dislike extremely, 5=neither like nor dislike, and 9=like extremely. The purchase intent was evaluated at the end of the sensory evaluation test. After completing the tetrad test and the acceptance tests, panelists were also asked their purchase intent of the green non-treated SFF cookie and pale brown-treated SFF cookie using a five-point scale from 1 ("would definitely not purchase") to 5 ("definitely would purchase") after seeing photos of the green non-treated SFF cookie and pale brown treated SFF cookie (FIG. 18).

Spread Ratio, Crude Fat, Moisture Content, pH, and Water Activity of Cookies

The spread ratio and moisture are factors that affect cookie greening. These parameters were measured in cookies that received enzyme treatment and in corresponding untreated controls. Size, moisture, and lipid content did not differ significantly (P>0.05) between treated and untreated cookies based on an analysis of variance test (ANOVA). Thus, these variables were excluded when assessing how the respective treatments affect greening in cookies.

Two additional variables that affect cookie color are pH and water activity/aw. pH differed between some treated vs. untreated cookies and therefore was included in subsequent models. High aw can increase color generating reactions, such as greening and Maillard browning by functioning as a diffusion medium. Since aw changed as cookies were stored over time, aw was therefore included in greening models.

CGA Esterase Activity in Cookies Made with Sunflower Butter

Figure 12:
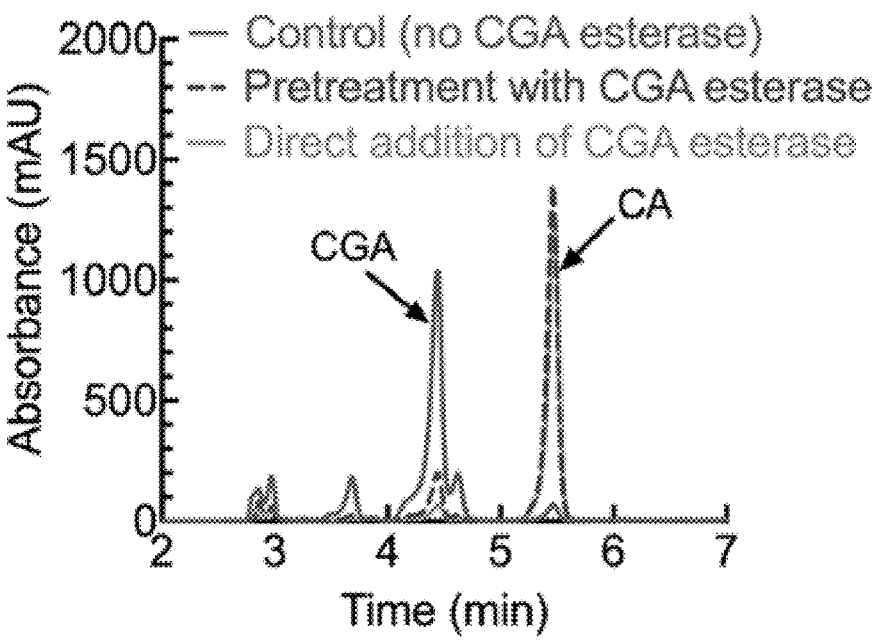
FIG. 12: HPLC chromatograms at 320 nm of sunflower flour cookies that received no CGA esterase (solid line), were pretreated with CGA esterase (dashed line), or directly treated with CGA esterase (solid line). The chromatograms for each sample are representative of three independent experiments.
Figure 13:
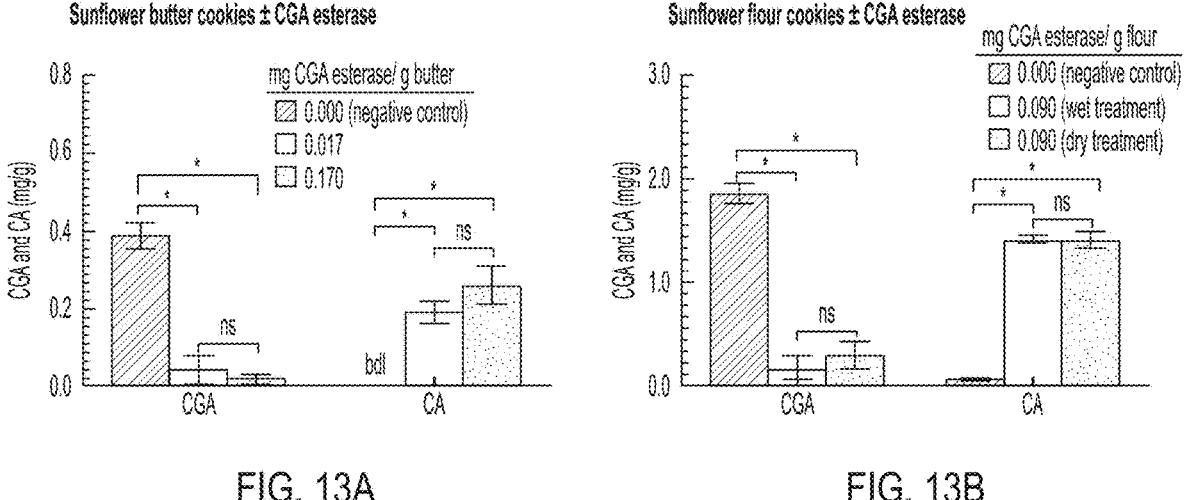
FIG. 13: CGA and CA levels in cookies where FIG. 13A CGA esterase was added to sunflower butter and FIG. 13B CGA esterase was added to sunflower flour before lyophilization (pretreatment) and after lyophilization (direct addition). Data was analyzed using ANOVA. Error bars show the standard deviation from the mean of two independent sets of dough formulations. * indicates significant difference at $P<0.05$ and bdl means below detection limit.

Previous work indicated that *L. helveticus* CGA esterase cleaves CGA in suspended sunflower meal and prevents greening in sunflower protein isolates (Example 1). Here, we tested whether CGA esterase is active in cookie dough made with SFB, which represents a more complex matrix. The enzyme was added directly to SFB, mixed with the other ingredients, and the dough was incubated for 10 min. CGA esterase was tested at two levels: $1.72 \times 10^{-1}$ mg/g and $1.72 \times 10^{-2}$ mg/g CGA esterase per gram of butter. These quantities were chosen based on the kinetic characterization of the enzyme (Example 1) and were expected to result in full cleavage of all CGA in 1 min and 10 min, respectively. FIGS. 12 and 13 show a significant decrease in the peak associated with CGA (retention time/RT=4.6 min) and a corresponding increase in the peak associated with caffeic acid (RT=5.5 min) at both enzyme levels. Both levels decreased CGA concentration equally by about 90-95% (FIG. 13A) and resulted in a concomitant increase in caffeic and quinic acids. The effectiveness of CGA esterase in SFB is notable since it suggests that the enzyme can be applied directly to the butter and is active in a lipid-rich dough. The high lipid content in the cookie dough does not appear to noticeably impact the activity of CGA esterase, mirroring the results of CGA esterase activity that were documented in undefatted sunflower seed meal (Example 1).

CGA Esterase Activity in Cookies Made with Sunflower Flour

This study further investigated how CGA esterase prevented greening in cookies made with SFF meal. CGA hydrolysis was carried out by either pretreating the flour or by directly adding the enzyme to the dough. For pretreatment, SFF was suspended in a buffered solution containing CGA esterase, and after 10 min enzymatic treatment, and the meal was lyophilized. The amount of enzyme for both pre- and direct treatment was 0.09 mg/g of flour, which was expected to result in complete CGA hydrolysis after 2 min. Enzyme addition resulted in nearly complete elimination of CGA, as shown in FIGS. 12 and 13B. CGA hydrolysis was accompanied by CA formation, further supporting the conclusion that CGA was hydrolyzed (FIG. 13B). Effective CGA hydrolysis in SFF for both direct and pretreated samples suggests that the enzyme does not need to operate in an aqueous environment. This finding is significant since it indicates that pretreatment of the flour, a process that involves a lengthy lyophilization step, is not necessary and that the enzyme can operate in non-aqueous environments such as cookie dough.

CGA Esterase Effect on Greening Sunflower Flour and Butter Cookies

Figure 14:
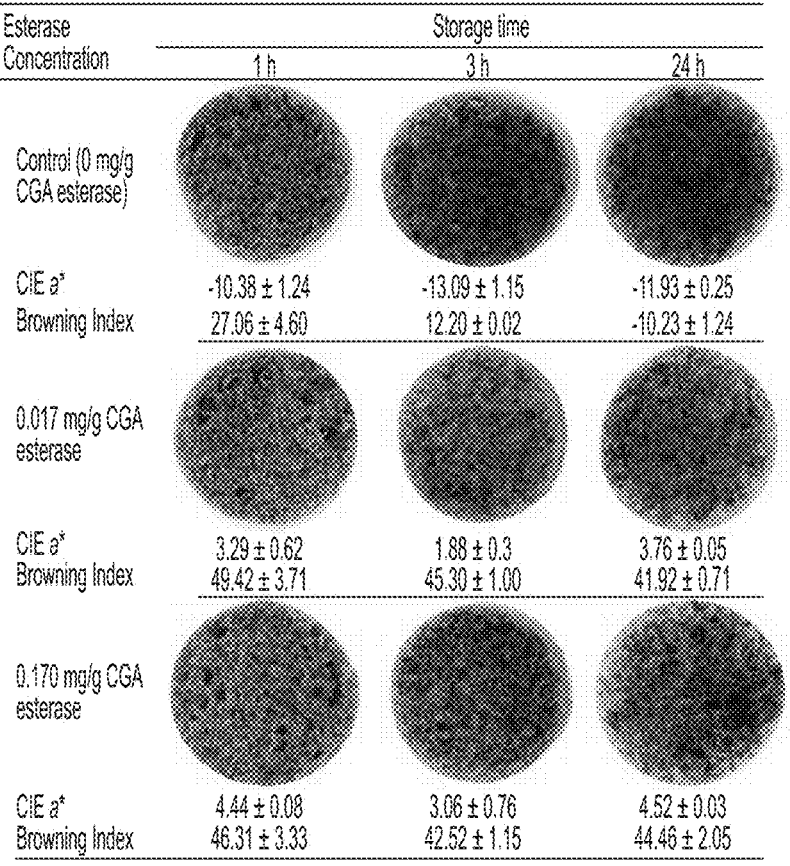
FIG. 14: Internal greening and browning of cookies formulated and baked with sunflower butter and varying concentrations of CGA esterase.

Cookies were baked with both treated SFB and SFF. Chlorogenic acid cleavage in esterase-treated cookies was strongly associated with decreased greening. As shown in FIGS. 14 and 15, and Tables 5, 6, 8, and 9, no greening occurred in either SFB or SFF cookies over the entire 24 h monitoring period that received CGA esterase. For both SFB and SFF cookies, greening was lower (higher a*) and only slightly time-dependent in CGA esterase containing cookies compared to untreated samples after controlling for the effects of pH and water activity. These data indicate that CGA hydrolysis-based greening prevention was successful.

TABLE 5

Effect of water activity, and pH on CIE a* values in sunflower butter cookies as a function of CGA esterase treatment. Folin-Ciocalteau's reducing capacity for each sample is also listed but not included in the statistical model.

| Time [hr] | Enzyme [$\times 10^{-2}$ mg/g] | Water activity | pH | CIE a* | FRC [µg/g] |
|---|---|---|---|---|---|
| 0 | 0 | 0.844 ± 0.020 | 8.71 ± 0.02 | −5.13 ± 0.32[d] | NA |
| | 1.72 | 0.808 ± 0.006 | 8.70 ± 0.06 | 3.97 ± 0.86[b] | NA |
| | 17.2 | 0.768 ± 0.008 | 8.79 ± 0.01 | 6.07 ± 0.07[a] | NA |

TABLE 5-continued

Effect of water activity, and pH on CIE a* values in sunflower butter cookies as a function of CGA esterase treatment. Folin-Ciocalteau's reducing capacity for each sample is also listed but not included in the statistical model.

| Time [hr] | Enzyme [×10⁻² mg/g] | Water activity | pH | CIE a* | FRC [μg/g] |
|---|---|---|---|---|---|
| 1 | 0 | 0.850 ± 0.001 | 8.91 ± 0.15 | −10.38 ± 1.24$^e$ | 65.13 ± 10.41 |
|  | 1.72 | 0.812 ± 0.003 | 8.84 ± 0.00 | 3.29 ± 0.62$^{bc}$ | 62.62 ± 0.51 |
|  | 17.2 | 0.790 ± 0.018 | 8.78 ± 0.06 | 4.44 ± 0.08$^b$ | 59.70 ± 8.73 |
| 3 | 0 | 0.803 ± 0.016 | 8.98 ± 0.02 | −13.09 ± 1.15$^f$ | 76.66 ± 8.10 |
|  | 1.72 | 0.815 ± 0.005 | 8.86 ± 0.00 | 1.88 ± 0.30$^c$ | 67.02 ± 19.59 |
|  | 17.2 | 0.798 ± 0.009 | 8.87 ± 0.02 | 3.07 ± 0.76$^{bc}$ | 57.48 ± 0.58 |
| 24 | 0 | 0.823 ± 0.028 | 9.07 ± 0.09 | −11.94 ± 0.25$^f$ | 66.40 ± 21.64 |
|  | 1.72 | 0.791 ± 0.018 | 9.00 ± 0.01 | 3.76 ± 0.05$^b$ | 41.02 ± 0.44 |
|  | 17.2 | 0.794 ± 0.008 | 8.94 ± 0.03 | 4.52 ± 0.03$^b$ | 39.49 ± 2.32 |

Values are reported as mean ± standard deviation. Values with different superscripts have significantly different means at P < 0.05.

TABLE 6

Effect of CGA esterase treatment, water activity, and pH on CIE a* values in sunflower flour cookies. Folin-Ciocalteau's reducing capacity for each sample is also listed but not included in the statistical model.

| Time [hr] | Flour Treatment | Water activity | pH | CIE a* | FRC [μg/g] |
|---|---|---|---|---|---|
| 0 | Control | 0.714 ± 0.018 | 6.36 ± 0.16 | 6.03 ± 0.06$^{bcd}$ | Not measured |
|  | Direct Treatment | 0.663 ± 0.016 | 6.40 ± 0.08 | 8.26 ± 0.42$^{abc}$ | Not measured |
|  | Pretreatment | 0.659 ± 0.016 | 6.79 ± 0.45 | 10.07 ± 0.53$^a$ | Not measured |
| 1 | Control | 0.693 ± 0.041 | 6.99 ± 0.13 | 4.80 ± 1.29$^d$ | 145.23 ± 17.37 |
|  | Direct Treatment | 0.685 ± 0.013 | 6.33 ± 0.21 | 8.95 ± 0.41$^{ab}$ | 154.57 ± 7.09 |
|  | Pretreatment | 0.688 ± 0.008 | 6.26 ± 0.10 | 9.67 ± 0.05$^a$ | 156.40 ± 11.10 |
| 3 | Control | 0.679 ± 0.036 | 6.44 ± 0.22 | 5.16 ± 1.31$^{cd}$ | 115.80 ± 21.48 |
|  | Direct Treatment | 0.648 ± 0.011 | 6.30 ± 0.10 | 8.66 ± 0.83$^{ab}$ | 168.30 ± 2.40 |
|  | Pretreatment | 0.653 ± 0.032 | 6.34 ± 0.03 | 9.69 ± 0.23$^a$ | 141.64 ± 1.06 |
| 24 | Control | 0.692 ± 0.023 | 7.62 ± 0.06 | −0.07 ± 0.69$^e$ | 117.35 ± 18.66 |
|  | Direct Treatment | 0.683 ± 0.009 | 7.28 ± 0.06 | 8.00 ± 0.56$^{abc}$ | 164.82 ± 5.92 |
|  | Pretreatment | 0.674 ± 0.020 | 7.48 ± 0.04 | 9.84 ± 1.25$^a$ | 152.67 ± 4.90 |

Values are reported as mean ± standard deviation. Values with different superscripts have significantly different means at P < 0.05.

TABLE 7

Diameter, height, spread ratio, fat content, and moisture of sunflower butter cookies chlorogenic acid (CGA) esterase. These data were analyzed by ANOVA, which showed that none of the parameters were affected by the respective treatments.

| Treatment | Diameter [mm] | Height [mm] | Spread ratio | Fat content [%] | Moisture content [% db] |
|---|---|---|---|---|---|
| Esterase Addition | | | | | |
| No esterase | 47.83 ± 1.41 | 22.49 ± 0.07 | 2.13 ± 0.06 | 19.60 ± 0.82 | 16.70 ± 0.54 |
| 1.72 × 10⁻² mg/g | 49.34 ± 0.94 | 22.26 ± 0.32 | 2.22 ± 0.07 | 19.42 ± 0.01 | 16.19 ± 0.07 |
| 1.72 × 10⁻¹ mg/g | 49.25 ± 0.35 | 23.87 ± 0.81 | 2.07 ± 0.08 | 19.45 ± 0.01 | 16.20 ± 0.84 |

TABLE 8

ANCOVA summary table for model describing the effects of pH, water activity, and chlorogenic acid esterase treatments on CIE a* for sunflower butter cookies (R2 = 0.999).

| | Df | Sum Sq | Mean Sq | F value | Pr(>F) |
|---|---|---|---|---|---|
| pH | 1 | 232.3 | 232.3 | 1856.19 | 1.09E−12 |
| aw | 1 | 352 | 352 | 2813.27 | 1.37E−13 |
| Time | 3 | 97.3 | 32.4 | 259.18 | 8.89E−10 |
| Trt_level | 2 | 443.5 | 221.7 | 1772.13 | 1.76E−13 |
| Time*Treatment Level | 6 | 19.5 | 3.2 | 25.93 | 1.52E−05 |
| Residuals | 10 | 1.3 | 0.1 | | |

TABLE 9

ANCOVA summary table for model describing the effects of pH, water activity, and chlorogenic acid esterase treatments on CIE a* for sunflower flour cookies (R2 = 0.971).

| | Df | Sum Sq | Mean Sq | F value | Pr(>F) |
|---|---|---|---|---|---|
| pH | 1 | 37.7 | 37.7 | 63.583 | 1.21E−05 |
| aw | 1 | 15.67 | 15.67 | 26.428 | 4.37E−04 |
| Time | 3 | 12.87 | 4.29 | 7.235 | 7.25E−03 |
| Trt level | 2 | 105.36 | 52.68 | 88.845 | 4.29E−07 |
| Tune*Treatment Level | 6 | 25.73 | 4.29 | 7.233 | 3.45E−03 |
| Residuals | 10 | 5.93 | 0.59 | | |

While enzymatic greening prevention worked in both SFF and SFB cookies, the effects on cookie color are different. The browning index increased substantially in SFB cookies (FIG. 14). Overall, in SFB cookies, the greenness of CGA-generated trihydroxy benzacridine compounds appears suitably mitigated (Table 6), however, excessive browning may still represent an aesthetic problem. Browning may arise from the hydrolysis product caffeic acid, which could autoxidize or be involved in Maillard reactions with proteins under alkaline conditions.

In SFF cookies, greening in untreated control cookies developed more slowly (FIG. 15 and Table 7). Initially, control cookies were not fully green. However, untreated cookies turn green over 24 hours, with a*values declining from 4.8 to −0.07. The lack of initial greenness likely is due to the more neutral pH inherent to these kinds of cookies (pH=6.18-7.66), which is maintained over time. CGA esterase treated cookies do not green at either enzyme application level as CIE a* values remain constant and positive over time (FIG. 15 and Table 7). Greening prevention occurs for both cookies that were made with pretreated and directly treated flour, reinforcing the conclusion that pretreatment is not necessary. Browning was higher in enzymatically treated SFF cookies than in untreated cookies (FIGS. 14 and 15). However, compared to cookies made with SFB, SFF cookies were lighter, and the color was more appealing. The SFF cookies formulated with CGA esterase were also much lighter than muffins that were made by Grasso and colleagues (Grasso et al., 2020) with baking powder and 15% or 30% sunflower flour. Baking powder does not alkalize the dough, unlike the baking soda used in this study. Furthermore, it is noteworthy that negative SFF control cookies were beginning to turn green over time despite being at neutral pH. Grasso and our results indicate that maintaining neutral or slightly acidic pH, in and of itself, is not sufficient to produce lightly colored cookies and that CGA esterase treatment represents a more effective method of greening prevention than pH modulation.

Folin Ciocalteu Reducing Capacity in CGA Esterase Treated Cookies

One of the key benefits of CGA esterase-based greening prevention of SFB and SFF over phenol extraction is that it maintains beneficial antioxidant phenolics. Tables 6 and 7 demonstrate the redox capacity of cookies, as measured by the Folin reducing capacity, is indistinguishable between treated and untreated cookies. These data confirm that hydrolysis-based greening mitigation does not change the overall Folin Ciocalteu reducing capacity in cookies.

Performance of CGA Esterase Activity Compared to Commercial Enzymes

Proximate and textural analysis of sunflower flour and sunflower flour cookies: The proximate composition of treated cookies, non-treated cookies, and SFF is shown in Table 10. The data indicate that moisture, protein, carbohydrate, ash, lipid, and texture (hardness and fracturability) between esterase-treated and non-treated cookies, were not statistically significant. As expected, the addition of CGA esterase to the SFF neither affected the macronutrient composition of the flour nor the texture of the cookies.

After the removal of approximately 42% of the total weight as fat during cold pressing, the lipid content of SFF after Soxhlet extraction was 7.56±0.64%. As shown in Table 1, the protein content for SFF was 35.69±0.31%. The protein content was higher than that found (27.80%) by Oliviera Filho (2021) and is higher than that of wheat flour which contains about 11.50% protein (Man et al., 2017). The protein content for treated and non-treated cookies was 20.80±1.66 and 21.13±3.80, respectively.

Since Liang & Were (2018) showed that high water activity and pH increase greening, they were also measured. Water activity was not significantly different in treated and non-treated cookies; however, the pH of esterase-treated cookies was lower by about 0.5 pH units, which is within the pH difference range reported in Pepra-Ameyaw et al. (2022) between enzymatically treated and non-treated cookies. CGA esterase-treated cookies are slightly less basic than non-treated cookies, most likely because CGA hydrolysis produces two acidic products, quinic acid, and caffeic acid, which have pKa values of 3.4 and 4.5, respectively. In contrast, CGA has a single acidic pKa of 3.6 (Kabir et al., 2014). While esterase-treated cookies were less basic than non-treated cookies, our previous work demonstrated that these small pH differences do not noticeably influence the greening, as there is greening in cookies at pH as low as 6.5.

TABLE 10

Proximate analysis of non-treated and treated cookies and of sunflower flour used in the sensory study. (bdl = below detection limit).

| | Non-treated cookies | Treated cookies | Sunflower Flour |
|---|---|---|---|
| Color | | | |
| L* | 35.55 ± 4.29 | 46.76 ± 0.47 | 82.94 ± 1.26 |
| a* | −2.40 ± 2.93 | 6.77 ± 0.27 | 1.33 ± 0.09 |
| b* | 13.10 ± 3.78 | 20.13 ± 0.80 | 10.42 ± 0.54 |
| Phenolic content (mg/g flour) | | | |
| Chlorogenic acid | 1.00 ± 0.04 | 0.13 ± 0.02 | 2.35 ± 0.24 |
| Caffeic acid | bdl** | 1.40 ± 0.13 | bdl** |
| Water activity | 0.54 ± 0.01 | 0.55 ± 0.01 | 0.45 ± 0.01 |
| pH | 7.69 ± 0.01 | 7.18 ± 0.02 | n/a |
| Proximates (%) | | | |
| Moisture | 7.12 ± 0.14 | 7.44 ± 0.09 | 7.32 ± 0.01 |
| Lipid | 23.03 ± 0.83 | 22.73 ± 0.14 | 7.56 ± 0.64 |
| Protein | 21.13 ± 3.80 | 20.80 ± 1.66 | 35.69 ± 0.31 |
| Ash | 3.51 ± 0.53 | 3.88 ± 0.01 | 6.05 ± 0.27 |
| Carbohydrate | 45.21 | 45.15 | 43.38 |

TABLE 10-continued

Proximate analysis of non-treated and treated cookies and of sunflower
flour used in the sensory study. (bdl = below detection limit).

|  | Non-treated cookies | Treated cookies | Sunflower Flour |
|---|---|---|---|
| Texture |  |  |  |
| Hardness | 1373.19 ± 46.04 | 1332.65 ± 21.52 | n/a |
| Fracturability | 1378.79 ± 20.70 | 1367.49 ± 18.94 | n/a |

Figure 16:
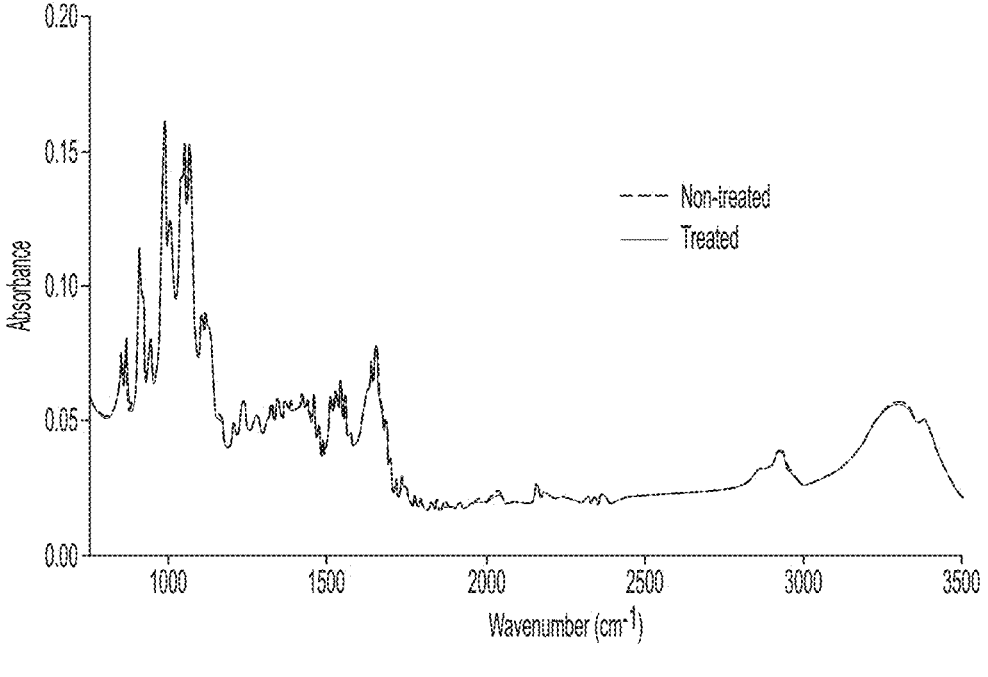
FIG. 16: Attenuated total reflectance Fourier transform infrared spectroscopy (ATR-FTIR) spectra of non-enzymatically treated and enzymatically treated cookies made with sunflower.

The structural properties of the macromolecules within the cookies were analyzed by ATR-FTIR (Ishii et al., 2021). The ATR-FTIR spectra of esterase-treated and non-treated cookies are shown in FIG. 16. The spectra are indistinguishable, indicating that esterase treatment does not alter the structure of lipids, proteins, or carbohydrates within the cookie. These data confirm previous results that *L. helveticus* CGA esterase is specific and does not act on biomolecules other than CGA to a noticeable degree (Lo Verd et al., 2022).

The activity of CGA esterase is consistent with our earlier work that demonstrated that CGA esterase was active in relatively crowded and dense sunflower meal suspensions, albeit with a lower $V_{max}$ compared to dilute solutions (Example 1). The amount of enzyme used in either SFF or SFB was low. In flour, 0.09 mg/g (90 ppm) of CGA esterase was used, whereas the lowest concentration applied to SFB was 0.0172 mg/g (17.2 ppm). These concentrations are comparable or well below those of commercially used hydrolases used in the baking industry, such as lipases, amylases, and xylanases, and suggest that use of *L. helveticus* CGA esterase is a feasible and efficient method of breaking down CGA in sunflower butter and flour to prevent greening. Utilizing CGA esterase would be compatible with clean label requirements as enzymes are widely accepted as safe for use in food processing.

CONCLUSIONS

CGA esterase is very effective at hydrolyzing CGA in both SFB and SFF, fully preventing greening in cookies containing either ingredient. The results from CGA esterase addition to SFB and SFF are, to the best of our knowledge, the first demonstration that SFB and SFF cookies can be made at alkaline pH without green color formation. Unlike existing greening prevention methods, dephenolization is not required, meaning that beneficial phenolic compounds remain in the SFB and SFF. Enzymatic CGA hydrolysis in SFF and SFB may enable more widespread use of sunflower-derived ingredients in high pH baking processes. Greater utilization of SFF would represent a valuable method of "upcycling" abundant sunflower meal that is produced during sunflower seed pressing and currently discarded or used as animal fodder.
Sensory Testing Results It was hypothesized that the sensory characteristics and composition of treated cookies would be identical to non-treated cookies, with the exception of the cookies' color since CGA esterase is not expected to react with any other components in the flour other than CGA. It was further hypothesized that color would be an important factor in consumer acceptance, with consumers preferring the CGA esterase-treated cookies to the green, non-treated cookies. Thus, the main objectives were to compare consumer acceptance between enzymatically treated and non-treated cookies using a 9-point hedonic scale, to examine the cookie's proximates, and to determine to what extent the color of cookies influenced consumer intent to purchase.

One hundred fifty-three untrained panelists participated in the study. Initially, panelists responded to a concept card describing the benefits of using SFF in baking (FIG. 17). This allowed us to gauge the initial consumer interest in cookies formulated with SFF. The responses from the concept card indicated that 40.9% of consumers would either "probably buy" or "definitely buy" a SFF cookie based on the nutritional information and/or the idea of "upcycling" (FIG. 17). Overall, the average rating was 3.27±0.88 on a 5-point scale. We did not, however, study which concept was the most important to panelists as all the attributes were placed within the same concept card. We realize that it would have been possible to determine the motivation behind panelists' decisions by providing one concept at a time as done by other researchers (Levis & Chambers IV, 1997; Mohayidin & Kamarulzaman 2014). However, such an investigation would not have been insightful in the current study since our exclusion criteria omitted any panelists with food sensitivities (allergies or intolerances to gluten, egg, etc.). This means that we would not have been able to gauge interest in sunflower flour as a baking ingredient from this key demographic group, who may find certain attributes in the concept card, e.g., being gluten- and soy-free, particularly important.

A 9-point hedonic rating test was used to determine panelists' liking of enzymatically treated versus non-treated cookies. The recipes for the non-treated and treated cookies were identical, except for adding 0.02 mg of enzyme per gram of flour in treated cookies. Table 10 shows the distribution (in terms of percentage) of panelists' responses to how much they like or dislike the smell, texture, and flavor and the overall acceptance of the cookie. We observe in Table 11 that the distribution of the percentage of panelists that like or dislike the sensory properties of the cookies was similar for both esterase treated and non-treated cookies. For instance, about 74% of the panelists gave a rating of "6=Like Slightly" to "9=Like Extremely" for the smell of non-treated cookies, while about 80% of the panelist gave a rating of "6=Like Slightly" to "9=Like Extremely" for the smell of the esterase-treated cookie. On the other hand, for the texture of the cookie, about 29% rated the non-treated cookie as "1=Dislike Extremely" to "4=Dislike Slightly", while 26% rated the enzymatically treated cookie as "1=Dislike Extremely" to "4=Dislike Slightly". This led to the hypothesis that the panelists do not like one cookie more than the other and that, generally, the two types of cookies received indistinguishable acceptance ratings. To verify this, we used a chi-squared test of independence to determine if there was an association between the consumers' ratings and the type of cookie for each sensory characteristic. The results of the chi-squared tests of independence (Table 11) supported the hypothesis that the panelists' responses in their liking of favor, texture, smell, and overall acceptability are independent of the type of cookie they consumed ($p>0.05$). This suggests that the panelists like treated and untreated cookies equally. Furthermore, these results strongly suggest that the difference identified in the tetrad test did not influence participants' ratings.

TABLE 11

Results from 9-point hedonic testing of non-treated and treated sunflower cookies.

| | Smell | | Texture | | Flavor | | Overall Acceptability | |
|---|---|---|---|---|---|---|---|---|
| | Control | Treatment | Control | Treatment | Control | Treatment | Control | Treatment |
| 1 = Dislike Extremely | 1.31% | 1.31% | 0.65% | 1.96% | 1.31% | 0.65% | 0.65% | 0.65% |
| 2 = Dislike Very Much | 0.00% | 1.31% | 1.31% | 1.31% | 0.65% | 0.00% | 0.65% | 0.65% |
| 3 = Dislike Moderately | 0.65% | 0.00% | 7.84% | 7.19% | 5.88% | 5.23% | 3.92% | 4.58% |
| 4 = Dislike Slightly | 11.11% | 3.92% | 18.95% | 15.69% | 15.03% | 10.46% | 15.03% | 7.84% |
| 5 = Neither Like nor Dislike | 13.07% | 13.73% | 9.80% | 6.54% | 14.38% | 9.15% | 13.73% | 10.46% |
| 6 = Like Slightly | 22.22% | 22.22% | 18.95% | 20.92% | 21.57% | 32.03% | 22.22% | 24.84% |
| 7 = Like Moderately | 24.84% | 29.41% | 26.14% | 24.18% | 27.45% | 26.80% | 29.41% | 30.72% |
| 8 = Like Very Much | 24.84% | 23.53% | 13.07% | 18.30% | 12.42% | 11.11% | 13.07% | 17.65% |
| 9 = Like Extremely | 1.96% | 4.58% | 3.27% | 3.92% | 1.31% | 4.58% | 1.31% | 2.61% |
| Chi-Squared Test of Independence (P-Value) | 0.23 | | 0.84 | | 0.23 | | 0.63 | |

The hedonic rating test results for texture are consistent with texture analyzer measurements, which determined that the enzyme did not impact hardness and fracturability (Table 1). Furthermore, these results are consistent with the proximates and ATR-FTIR measurements suggesting that CGA esterase does not participate in side reactions with other macromolecules that could negatively affect the cookie's sensory properties. Overall, these results confirm that enzymatic treatment does not influence consumer perceptions of the cookie regarding texture, flavor, smell, and overall acceptability.

Figure 19:
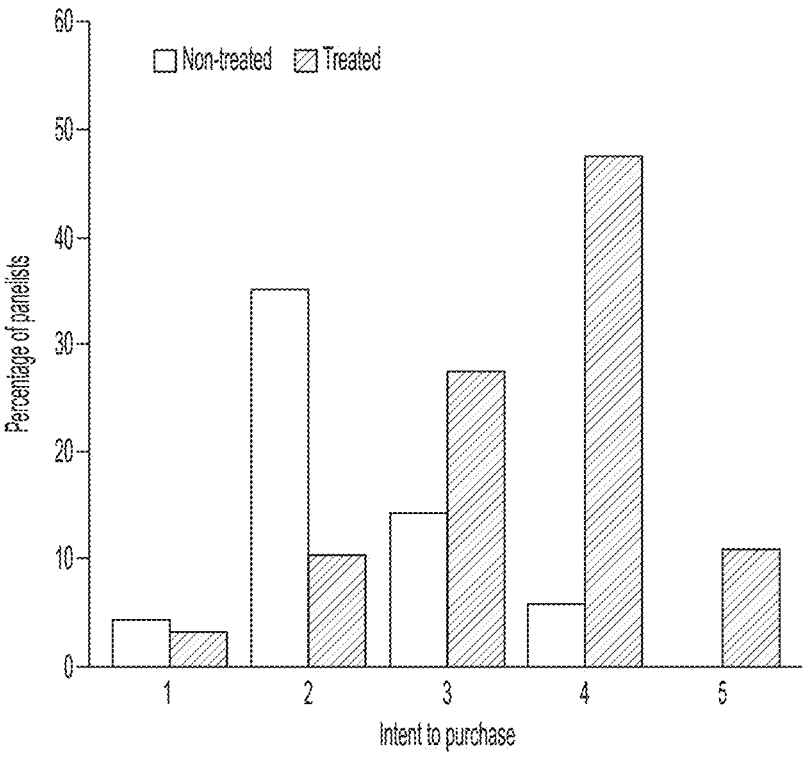
FIG. 19: Panelists' responses to the concept card. Panelists rated their intent to purchase on a 5-point scale where 1="definitely would not buy", 2="probably would not buy", 3="might or might not buy", 4="probably would buy", 5="definitely would buy".

Intent to purchase: Panelists were asked if CGA esterase treatment of SFF cookies affected the intent to purchase based on cookie color (FIG. 18). FIG. 20 indicates that color influences purchasing intent, as 79.7% of panelists stated that they "probably would not" or "definitely would not" purchase untreated, green-colored cookies. In contrast to untreated cookies, only 13.7% of panelists "probably would not" or "definitely would not" buy the enzymatically treated, pale brown colored cookies. Furthermore, 58.8% of panelists indicated that they "probably would purchase" or "definitely would purchase" esterase-treated SFF cookies, while only 5.9% of panelists indicated that they "probably would purchase" or "definitely would purchase" the non-treated SFF cookies (FIG. 19). A test of equality of two proportions showed that the proportion of panelists that "probably would" or "definitely would" purchase esterase-treated SFF cookies is significantly greater than the proportion of panelists that "probably would" or "definitely would" purchase the green non-treated SFF cookies ($p<0.05$). These data strongly suggest that enzymatic hydrolysis of CGA in SFF increases general consumer acceptability.

REFERENCES

Atonfack, J. T., Ataman, Z. A., & Were, L. M. (2019). Acidulant effect on greening, reducing capacity, and tryptophan fluorescence of sunflower butter cookie dough during refrigerated storage. *J. Sci. Food. Agric.*, 99 (5), 2186-2193.

Benoit, I., Asther, M., Bourne, Y., Navarro, D., Canaan, S., Lesage-Meessen, L., Herweijer, M., Coutinho, P. M., Asther, M., & Record, E. (2007). Gene overexpression and biochemical characterization of the biotechnologically relevant chlorogenic acid hydrolase from *Aspergillus niger. Appl Environ Microbiol*, 73 (17), 5624-5632.

Chahinian, H., Ali, Y. B., Abousalham, A., Petry, S., Mandrich, L., Manco, G., Canaan, S., & Sarda, L. (2005). Substrate specificity and kinetic properties of enzymes belonging to the hormone-sensitive lipase family: comparison with non-lipolytic and lipolytic carboxylesterases. *Biochim Biophys Acta*, 1738 (1-3), 29-36.

Fritsch, C., Jansch, A., Ehrmann, M. A., Toelstede, S., & Vogel, R. F. (2017). Characterization of Cinnamoyl Esterases from Different Lactobacilli and Bifidobacteria. *Curr Microbiol*, 74 (2), 247-256.

Gonzalez-Perez, S., Merck, K. B., Vereijken, J. M., van Koningsveld, G. A., Gruppen, H., & Voragen, A. G. (2002). Isolation and characterization of undenatured chlorogenic acid free sunflower (*Helianthus annuus*) proteins. *J Agric Food Chem*, 50 (6), 1713-1719.

Grasso, S., Liu, S. Y., & Methven, L. (2020). Quality of muffins enriched with upcycled defatted sunflower seed flour. *Lwt-Food Science and Technology*, 119.

Ishii, A. K., Toto Pacioles, C., & Were, L. (2021). Color and structural modifications of alkaline extracted sunflower protein concentrates and isolates using L-cysteine and glutathione. *Food Res Int,* 147, 110574.

Kumar, R. S., Brannigan, J. A., Prabhune, A. A., Pundle, A. V., Dodson, G. G., Dodson, E. J., & Suresh, C. G. (2006). Structural and functional analysis of a conjugated bile salt hydrolase from *Bifidobacterium longum* reveals an evolutionary relationship with penicillin V acylase. *J Biol Chem,* 281 (43), 32516-32525.

Lai, K. K., Lorca, G. L., & Gonzalez, C. F. (2009). Biochemical Properties of Two Cinnamoyl Esterases Purified from a *Lactobacillus johnsonii* Strain Isolated from Stool Samples of Diabetes-Resistant Rats. App/*Environ Microbiol,* 75 (15), 5018-5024.

Lai, K. K., Stogios, P. J., Vu, C., Xu, X., Cui, H., Molloy, S., Savchenko, A., Yakunin, A., & Gonzalez, C. F. (2011). An Inserted alpha/beta Subdomain Shapes the Catalytic Pocket of *Lactobacillus johnsonii* Cinnamoyl Esterase. *PLoS One,* 6 (8).

Liang, S., Tran, H. L., & Were, L. (2018). Lowering greening of cookies made from sunflower butter using acidic ingredients and effect on reducing capacity, tryptophan and protein oxidation. *Food Chem,* 252, 318-326.

Liang, Y., & Were, L. (2020). Cysteine's effects on chlorogenic acid quinone induced greening and browning: Mechanism and effect on antioxidant reducing capacity. *Food Chem,* 309, 125697.

Medina, M. S., Bretzing, K. O., Aviles, R. A., Chong, K. M., Espinoza, A., Garcia, C. N. G., Katz, B. B., Kharwa, R. N., Hernandez, A., Lee, J. L., Lee, T. M., Lo Verde, C., Strul, M. W., Wong, E. Y., & Owens, C. P. (2021). CowN sustains nitrogenase turnover in the presence of the inhibitor carbon monoxide. *J Biol Chem,* 296, 100501.

Pickardt, C., Neidhart, S., Griesbach, C., Dube, M., Knauf, U., Kammerer, D. R., & Carle, R. (2009). Optimisation of mild-acidic protein extraction from defatted sunflower (*Helianthus annuus* L.) meal. *Food Hydrocoll.,* 23 (7), 1966-1973.

Singleton, R., V., & Rossi, A. J. (1965). Colorimetry of total phenolics with phosphomolybdic-phosphotungstic acid reagents. *Am J Enol Vitic,* 14, 144-158.

Song, Y. R., & Baik, S. H. (2017). Molecular cloning, purification, and characterization of a novel thermostable cinnamoyl esterase from *Lactobacillus helveticus* KCCM 11223. *Prep. Biochem. Biotechnol.,* 47 (5), 496-504.

Wianowska, D., & Gil, M. (2019). Recent advances in extraction and analysis procedures of natural chlorogenic acids. *Phytochemistry Rev.,* 18, 273-302.

Zhang, W. B., Liu, Y. C., Hu, M. J., & Yang, R. J. (2019). Preparation of high-quality sunflower seed protein with a new chlorogenic acid hydrolase from *Aspergillus niger. Biotechnol. Lett.,* 41 (4-5), 565-574.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

SEQUENCE LISTING

This application contains a sequence listing having the filename 1959206-00036_Sequence_Listing.xml, which is 8 KB in size, and was created on Jun. 29, 2023. The entire content of this sequence listing is incorporated herein by reference.

---

SEQUENCE LISTING

```
Sequence total quantity: 6
SEQ ID NO: 1              moltype = DNA   length = 34
FEATURE                   Location/Qualifiers
source                    1..34
                          mol_type = other DNA
                          organism = synthetic construct
SEQUENCE: 1
gcccgctagc atgagccgca ttaccattga acgc                             34

SEQ ID NO: 2              moltype = DNA   length = 36
FEATURE                   Location/Qualifiers
source                    1..36
                          mol_type = other DNA
                          organism = synthetic construct
SEQUENCE: 2
ccgcgagctc ttaaaacgcc ggtttcagaa actgcg                           36

SEQ ID NO: 3              moltype = AA   length = 248
FEATURE                   Location/Qualifiers
source                    1..248
                          mol_type = protein
                          organism = Lactobacillus johnsonii
SEQUENCE: 3
MATTITLERD GLQLVGTREE PFGEIYDMAI IFHGFTANRN TSLLKEIANS LRDENIASVR  60
FDFNGHGDSD GKFENMTVLN EIEDANAILN YVKTDPHVRN IYLVGHSQGG VVASMLAGLY  120
PDLIKKVVLL APAATLKSDA LEGNTQGVTY NPDHIPDRLP FKDLTLGFYL RIAQQLPIYE  180
VSAQFTKPVC LIHGTDDTWS PNASKKYDQI YQNSTLHLIE GADHCFSDSY QKNAVNLTTD  240
FLQNNNAF                                                          248

SEQ ID NO: 4              moltype = AA   length = 258
FEATURE                   Location/Qualifiers
source                    1..258
                          mol_type = protein
                          organism = Lactobacillus gasseri
SEQUENCE: 4
MKLKKKKVGI YMATITIERD GLNLVGTREE PFGEIYDMAI IFHGFTANRN TPLLKEIADE  60
LRDENIASVR FDFNGHGDSD GKFENMTVLN EIEDANAILN YVKTDPHVRN IYLVGHSQGG  120
VVASMLAGLY PDIIKKVVLL APAATLKTDA LNGSTQGVKY NPDHIPDRLP FKDLTLGFYL  180
RIAQQLPIYE VSVHFTRPVC LIHGANDTWS PDASKKYDQV YENSTLHLVE GADHSFTDTY  240
QKTAADLTAE FLQDNNTF                                               258

SEQ ID NO: 5              moltype = AA   length = 249
FEATURE                   Location/Qualifiers
source                    1..249
                          mol_type = protein
                          organism = Lactobacillus helveticus
SEQUENCE: 5
MSRITIERDG LTLVGDREEP FGEIYDMAII MHGFAANRNT DLLRQIADDL RDENVASVRF  60
DFNGHGESDG KFEDMTVCNE IADGKAILDY VRTDPHVRDI FLVGHSQGGV VASMLAGLYP  120
DVVKKVVLLA PAAQLKDDAL RSNTQGATYD PNHIPDWPLV GNKLGMKLGG FYLRTAQVLP  180
IYEVSQCFTR PVSVIAGTND QWDPKYAKKY DEVYENSELH MIPNADHRFS GGYKDMAADL  240
TAQFLKPAF                                                         249

SEQ ID NO: 6              moltype = AA   length = 246
FEATURE                   Location/Qualifiers
source                    1..246
                          mol_type = protein
                          organism = Lactobacillus acidophilus
SEQUENCE: 6
MSRITIERDG LTLVGDREEP FGEIYDMAIL MHGFTANRNT PLLRQIADNL RDENVASVRF  60
DFNGHGESDG AFEDMTVCNE IADAQKILEY VRTDPHVRNI FLVGHSQGGV VASMLAGLYP  120
DIVKKVVLLA PAAQLKDDAL NGDTQGATYN PEHIPAAIPF HGKKLGGFYL RTAQVLPIYE  180
IAKHYTNPVS IIVGSNDQWA PKYSKKYDEV YENSELHMVP DADHSFTGQY KDSAVDLTAE  240
FLKPLF                                                            246
```

What is claimed is:

1. A method of hydrolyzing chlorogenic acid (CGA) in a sunflower seed-containing product comprising treating the sunflower seed-containing product with a CGA esterase of SEQ ID NO: 5 (*Lactobacillus helveticus*) and/or SEQ ID NO: 6 (*Lactobacillus acidophilus*).

2. The method of claim 1, wherein the sunflower seed-containing product comprises sunflower meal, sunflower butter, or a sunflower protein product.

3. The method of claim 1, wherein the treating comprises contacting a dough containing sunflower meal, sunflower butter, or sunflower protein product with the CGA esterase or contacting the sunflower meal, sunflower butter, or sunflower protein product directly.

4. The method of claim 1, wherein treatment of the sunflower seed-containing product with the CGA esterase lessens the greening of bakery goods produced from the sunflower seed-containing product.

5. The method of claim 1, wherein the CGA esterase is of SEQ ID NO: 5 (*Lactobacillus helveticus*).

6. The method of claim 1, wherein said treating comprises addition of less than 100 ppm of CGA esterase to the sunflower seed-containing product.

7. The method of claim 1, wherein the sunflower seed-containing product is incorporated into a food product.

8. The method of claim 7, wherein the sunflower seed-containing product is incorporated into a baked food product.

9. The method of claim 8, wherein the baked food product comprises cookies, bread, or muffins.

10. The method of claim 1, wherein the sunflower seed-containing product is sunflower butter.

11. The method of claim 1, wherein the sunflower seed-containing product is sunflower flour.

12. The method of claim 1, wherein one or more sensory qualities are improved in the treated sunflower-seed containing product when compared to a non-treated sunflower seed containing product.

13. The method of claim 12, wherein the one or more sensory qualities are smell, texture, color, appearance, taste, pH, or a combination thereof.

14. The method of claim 5, wherein the CGA esterase of SEQ ID NO: 5 (*Lactobacillus helveticus*) has a $V_{max}$ of $170.2 \pm 32.3$ mM $min^{-1}$ $mg^{-1}$ and a $K_m$ of $0.098 \pm 0.038$ mM.

15. The method of claim 5, wherein the CGA esterase of SEQ ID NO: 5 (*Lactobacillus helveticus*) is purified as a dimer with a molecular weight of approximately 60 kDa.

16. The method of claim 5, wherein the CGA esterase of SEQ ID NO: 5 (*Lactobacillus helveticus*) is structurally stable up to a temperature of 65° C. in a pH range from 6.0 to 9.0.

17. The method of claim 5, wherein the CGA esterase of SEQ ID NO: 5 (*Lactobacillus helveticus*) remains active until at least 50° C.

18. The method of claim 5, wherein the CGA esterase of SEQ ID NO: 5 (*Lactobacillus helveticus*) completely hydrolyzes CGA in the sunflower seed-containing product, wherein the sunflower seed-containing product is sunflower meal.

19. The method of claim 18, wherein the sunflower meal is undefatted sunflower meal or defatted sunflower meal.

20. The method of claim 1, wherein the CGA esterase is of SEQ ID NO: 6 (*Lactobacillus acidophilus*).

* * * * *